US011679080B2

(12) United States Patent
McDonnell et al.

(10) Patent No.: US 11,679,080 B2
(45) Date of Patent: *Jun. 20, 2023

(54) STARCH-FREE SOFT CHEW FOR VETERINARY APPLICATIONS

(71) Applicant: TGX SOFT CHEW, LLC, Wilmington, DE (US)

(72) Inventors: Kevin McDonnell, Lefaivre (CA); Joanna Rossi, Pincourt (CA); Scott Eccles, Deux Montagnes (CA); Gueorgui Puchkarov, Saint-Laurent (CA)

(73) Assignee: TGX SOFT CHEW, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,680

(22) Filed: Aug. 23, 2022

(65) Prior Publication Data
US 2022/0401357 A1    Dec. 22, 2022

Related U.S. Application Data

(63) Continuation of application No. 16/564,880, filed on Sep. 9, 2019, now Pat. No. 11,478,421, which is a continuation of application No. PCT/IB2018/055519, filed on Jul. 24, 2018.

(60) Provisional application No. 62/537,273, filed on Jul. 26, 2017.

(51) Int. Cl.
*A61K 9/00* (2006.01)
*A61K 47/38* (2006.01)
*A61K 47/26* (2006.01)
*A61K 9/16* (2006.01)
*A61K 47/12* (2006.01)
*A61K 45/06* (2006.01)

(52) U.S. Cl.
CPC .......... *A61K 9/0056* (2013.01); *A61K 9/1611* (2013.01); *A61K 9/1623* (2013.01); *A61K 9/1635* (2013.01); *A61K 47/12* (2013.01); *A61K 47/26* (2013.01); *A61K 47/38* (2013.01); *A61K 45/06* (2013.01)

(58) Field of Classification Search
None
See application file for complete search history.

(56) References Cited

U.S. PATENT DOCUMENTS 11,478,421 B2 * 10/2022 McDonnell .......... A61K 31/352

* cited by examiner

*Primary Examiner* — Jake M Vu
(74) *Attorney, Agent, or Firm* — Bishop, Diehl & Lee, Ltd.

(57) ABSTRACT

The present invention relates to a starch-free soft chew formulation for oral delivery of at least one active ingredient to an animal, and a starch-free soft chew containing the formulation and at least one active ingredient. The starch-free soft chew includes one or more active ingredients and excipients, such as a bulking agent, a flavoring agent, a humectant, a preservative, an antioxidant, and a lubricant, but no added water. In addition, the invention relates to a composition of starch-free, non-water excipients for use in the final dosage form of a soft chew for oral administration of at least one active ingredient to an animal. Also provided are processes for making the starch-free soft chew formulation and the starch-free soft chew.

21 Claims, 5 Drawing Sheets

STARCH-FREE SOFT CHEW FOR VETERINARY APPLICATIONS

RELATED APPLICATIONS

This application is a continuation of U.S. patent application Ser. No. 16/564,880 titled "STARCH-FREE SOFT CHEW FOR VETERINARY APPLICATIONS" and filed on Sep. 9, 2019, which is a continuation of International Application No. PCT/IB2018/055519 also titled "STARCH-FREE SOFT CHEW FOR VETERINARY APPLICATIONS and filed Jul. 24, 2018, which in turn claims the benefit of U.S. Provisional Application No. 62/537,273 filed on Jul. 26, 2017. The entire contents of each of the three above-listed applications are hereby incorporated by reference.

TECHNICAL FIELD

The present invention relates to soft chews in general, and in particular to starch-free soft chew compositions and processes for preparing such compositions that are suitable for animals and veterinary applications.

BACKGROUND

Chewable compositions suitable for oral delivery of pharmaceutical compounds and other medicaments are well known. Many pharmaceutical compounds that are otherwise unpalatable as a result of unacceptable taste due to factors such as acidity, bitterness, tingling or burning of the throat, or tastelessness, can often be made palatable by suitable coatings, capsules, or flavoring agents. In the veterinary context, chewable compositions (with suitable flavoring agents, if needed) are preferred because it can be challenging to encourage an animal to swallow a whole tablet or capsule.

Some chewable pharmaceutical products currently on the market for animals fail to have desirable physicochemical attributes (e.g., they have high water content, hard texture, slow disintegration, poor dissolution in physiologically relevant media, etc.). Older soft chewable pharmaceutical products on the market for animals, which show poor in-vitro disintegration and dissolution, would not meet the current United States Food and Drug Administration (FDA) regulations for in-vitro dissolution. Only recently have regulatory bodies begun to require that the dissolution of the drug product be tested using a discriminating in-vitro dissolution method. A discriminating dissolution method should be able to detect changes in the formulation, raw material attributes, and process parameters during the manufacture of the drug product. Hence, a new soft chewable formulation that can meet the regulatory agencies' requirements for dissolution in physiologically relevant media is needed.

Many patents related to chewable compositions exist. For example, U.S. Pat. No. 5,637,313 discloses is a soft, chewable dosage form, including a matrix of hydrogenated starch hydrolysate, a water-soluble bulking agent, and a water insoluble bulking agent. The patent also discloses a method of preparing a soft, chewable dosage form, including the steps of mixing under high shear force, a hydrogenated starch hydrolysate, a water-soluble bulking agent, and a water insoluble bulking agent.

The importance of water for the stability of chewable oral delivery systems has been recognized. Controlling the water within a product influences not only microbial spoilage but also chemical and physical stability. U.S. Pat. No. 6,387,381 discloses a carrier formed of a matrix having starch, sugar, fat, polyhydric alcohol, and water in suitable ratios. This patent explains that controlling water activity in an oral delivery system is its main object; it describes that the water activity of the product matrix may be adjusted up or down so that the availability of water in the finished product is not detrimental to the included active ingredient, be it pharmaceutical, nutraceutical, or a vitamin mineral complex.

U.S. Pat. No. 7,955,632 discloses a palatable, edible soft chewable medication vehicle for delivery of a pharmaceutically acceptable active ingredient, such as a drug, to an animal or human subject. The edible soft chews contain only food grade or better inactive ingredients, including various starches, and preferably do not contain ingredients of animal origin. Processes for manufacturing the edible soft chews do not require the use of heat during mixing of active and inactive ingredients and the disclosure claims to provide stable concentrations of the active ingredient and produce chews of consistent weight and texture.

U.S. Pat. No. 8,541,019 discloses a palatable ductile chewable veterinary composition for oral administration. The composition is capable of killing endo-parasites and ecto-parasites and/or can be used for treating prophylactic or curative animal diseases, and it is useful for the treatment of any warm-blooded non-human animal, including herd animals, like horses, cattle, sheep, or poultry and preferably pets like dogs and cats. It consists basically of an effective amount of one or more ingredients that are active against animal pests, pathogens, or animal diseases, meat flavoring, partially gelatinized starch, a softener, and up to 9% water. According to the patent, if the mixture of excipients and active ingredient does not contain moisture, water should be added during the extrusion process to improve flexibility of the chewable veterinary composition.

As noted above, while several patents discuss palatable chewable oral dosage forms for delivery of pharmaceutical ingredients to animals, there still exists a need to produce soft chews for animals that meet the current FDA requirements for dissolution testing, particularly the FDA's requirement that a drug product be tested using a discriminating dissolution method. In addition, existing chewable oral dosage forms for the delivery of pharmaceutical ingredients to animals contain starch as a necessary ingredient. Starch is a pharmaceutical excipient well known to have high moisture content. The high level of moisture contained within starch makes it unsuitable for use in drug formulations for which moisture content must remain consistent, including formulations of moisture-sensitive drugs.

Accordingly, although chewable compositions are known, improvements are desired, especially in connection with the stability of soft chew products and the development of discriminatory dissolution methods for testing same.

SUMMARY

As described herein, the inventors sought to develop a palatable soft chew oral dosage form for administering pharmaceuticals or nutraceuticals to animals that could avoid some of the challenges of existing soft chews. For instance, the inventors sought to prepare a soft chew that would meet the FDA requirements for dissolution in physiologically relevant media. They also sought to develop a soft chew that has low water content and remains suitable for moisture-sensitive active ingredients. It is thus an object of the present invention to provide an improved soft chew composition and a process for preparing such a composition that is suitable for administration of medicaments and other active ingredients to animals.

As discussed in greater detail below, the inventors have developed a soft chew oral dosage form that contains no starch and no water added to the process. With these features, the inventors' soft chew is particularly suitable for moisture-sensitive drugs.

In accordance with one aspect of the present invention, there is provided a soft chew that includes one or more pharmaceutically-active or nutritionally-active ingredients and a plurality of excipients. The soft chew contains no added water and the plurality of excipients contain no starch. The excipients may include a filler, a flavoring agent or palatant, a humectant, a solvent, a softening agent, a preservative, an antioxidant, and a lubricant. In one implementation, the plurality of excipients include at least two dry or solid ingredients and at least two wet or liquid ingredients. In another implementation, the solid ingredients do not include starch as an excipient and the liquid ingredients do not include water as an excipient. In yet another implementation, the solid ingredients at least include dibasic calcium phosphate (e.g., anhydrous, monohydrous, or dihydrous) and microcrystalline cellulose, the liquid ingredients at least include glycerin and medium chain triglycerides, and the soft chew contains no added water and the filler contains no starch. In yet another implementation, the plurality of excipients further includes at least one flavoring agent. In still yet another implementation, the plurality of excipients is pharmaceutical-grade.

In accordance with another aspect of the present invention, there is provided a process for making a soft chew. The process includes dry mixing a plurality of dry ingredients, in a mixer; wet massing by adding a plurality of liquid ingredients into the mixer into a dough-like material; forming the dough-like material into ribbon; portioning the ribbon into a predetermined length of soft chew portions; and packaging the soft chew portions. The dry ingredients do not include starch as an excipient and the liquid ingredients do not include water as an excipient.

In accordance with another aspect of the present invention, there is provided a starch-free composition of excipients for a final dosage in the form of a soft chew that does not necessitate the use of starch or added water. In one implementation, the starch-free composition of excipients includes at least two solid ingredients and at least two liquid ingredients. In another implementation, the solid ingredients do not include starch as an excipient and the liquid ingredients do not include water as an excipient. In another implementation, the solid ingredients at least include dibasic calcium phosphate dihydrate and microcrystalline cellulose, the liquid ingredients at least include glycerin and medium chain triglycerides, and no starch or added water is required. In yet another implementation, the starch-free composition of excipients is a vehicle for oral administration of a pharmaceutically-active ingredient that is moisture-sensitive. In yet another implementation, the starch-free composition of excipients further includes at least one flavoring agent. In still another implementation, all excipients are pharmaceutical-grade.

In another aspect, the invention relates to a soft chew that includes a pharmaceutically-active ingredient and a plurality of excipients. In certain implementations, the soft chew contains no added water and the plurality of excipients contains no starch.

In one implementation, the plurality of excipients in the soft chew includes a filler, a flavoring agent, a humectant, a solvent, a softening agent, a preservative, an antioxidant, and a lubricant. Exemplary fillers include dibasic calcium phosphate dihydrate (DiCal), microcrystalline cellulose (MCC), lactose, and any combination of any of the foregoing. In one exemplary implementation, the filler is dicalcium phosphate dihydrate at 15-90% w/w of the soft chew. Exemplary solvents include caprylic/capric triglyceride, medium chain triglyceride (MCT), long-chain triglycerides (LCT), and any combination of any of the foregoing. Exemplary softening agents include magnesium stearate, stearic acid, sodium stearyl fumarate, and any combination of any of the foregoing.

In another implementation, the plurality of excipients can further include a binder and/or disintegrant and/or surfactant. Exemplary binders include povidone, hydroxyl propyl cellulose (HPC), hydroxyl methyl cellulose (HPMC), and any combination of any of the foregoing.

In one exemplary implementation, the soft chew includes: 15-90% w/w dicalcium phosphate dihydrate; 5-30% w/w flavoring; 5-40% w/w microcrystalline cellulose; 0-15% w/w croscarmellose sodium; 0-5% w/w sodium stearyl fumarate; 15-50% w/w glycerin; 15-50% w/w medium chain triglycerides; 0-5% w/w citric acid anhydrous; 0.01-3% w/w potassium sorbate; and 0.01-3% w/w DL-α-tocopheryl acetate.

In another aspect, the invention relates to a process for making the soft chew by: (a) dry-mixing a plurality of dry ingredients, in a mixer; (b) wet-massing by adding a plurality of liquid ingredients into the mixer into a dough-like material; (c) forming the dough-like material into ribbon; (d) portioning the ribbon into a predetermined length of soft chew portions; and (e) packaging the soft chew portions.

In one implementation of the process, the plurality of dry ingredients includes at least one pharmaceutically-active ingredient. In another implementation of the process, the plurality of liquid ingredients includes at least one pharmaceutically-active ingredient.

In further implementations of the process, the plurality of dry ingredients include at least one of a filler, a flavoring agent, a humectant, a solvent, a softening agent, a preservative, an antioxidant, and a lubricant, and the plurality of liquid ingredients include at least one of a filler, a flavoring agent, a humectant, a solvent, a softening agent, a preservative, an antioxidant, and a lubricant.

In one implementation of the process, the mixer can be a low shear mixer or a high shear mixer. In another implementation of the process, the cutting can be performed using a portioning tool.

In another aspect, the invention relates to a starch-free soft chew formulation for oral delivery of at least one active ingredient to an animal. In certain implementations the soft chew formulation includes a plurality of starch-free excipients. These starch-free excipients can include, for example, non-starch solid excipients and non-water liquid excipients. Some implementations include at least two non-starch solid excipients and at least two non-water liquid excipients. In some implementations, the soft chew formulation is made without adding water as an excipient.

Exemplary starch-free excipients for use in the soft chew formulation include, without limitation, at least one filler, a humectant, a solvent, a softening agent, and a lubricant. In some implementations, the plurality of starch-free excipients includes at least two fillers. In some implementations, the plurality of starch-free excipients further includes at least one of a flavoring, a binder, a disintegrant, and a surfactant.

In some implementations of the soft chew formulation, the at least two non-starch solid excipients include dibasic calcium phosphate and microcrystalline cellulose. In some implementations, the at least two non-starch solid excipients include dibasic calcium phosphate, microcrystalline cellulose, and lactose (e.g., lactose monohydrate.). Exemplary dibasic calcium phosphates suitable for the soft chew formulation include, without limitation, hydrous dibasic calcium phosphates, such as dibasic calcium phosphate dihydrate, and the like. In some implementations, the weight ratio of dibasic calcium phosphate to microcrystalline cellulose is about 1:1-4:1 or about 2:1-3:1.

In some implementations of the soft chew formulation, the at least two non-water excipients include glycerin and triglycerides of fatty acids with carbon chain lengths of C6-C12. Exemplary triglycerides of fatty acids suitable for the soft chew formulation include, without limitation, caprylic/capric triglycerides and medium-chain triglycerides. In some implementations, the weight ratio of glycerin to the triglycerides of fatty acids is about 4:1 to 7:1 or about 5:1 to 6:1.

In some implementations, the soft chew formulation also includes one or more of croscarmellose sodium; magnesium stearate, stearic acid, or sodium stearyl fumarate; citric acid (e.g., citric acid anhydrous); potassium sorbate; α-tocopherol (e.g., DL-α-tocopheryl acetate); and povidone, hydroxyl propyl cellulose, or hydroxyl methyl cellulose.

In some implementations of the soft chew formulation, the plurality of starch-free excipients includes dibasic calcium phosphate dihydrate, microcrystalline cellulose, glycerin, and medium-chain triglycerides. In some implementations, the weight ratio of dibasic calcium phosphate dihydrate to microcrystalline cellulose is about 2:1 to about 3:1. In some implementations, the weight ratio of glycerin to medium-chain triglycerides is about 5:1 to 6:1.

In one implementation, the soft chew formulation includes: dibasic calcium phosphate dihydrate; microcrystalline cellulose; flavoring; croscarmellose sodium; glycerin; medium-chain triglycerides; and magnesium stearate or sodium stearyl fumarate. By way of example, the soft chew formulation includes, in certain implementations, dibasic calcium phosphate dihydrate, microcrystalline cellulose, flavoring, croscarmellose sodium, glycerin, medium-chain triglycerides, and magnesium stearate, in a weight ratio of about 25:8:30:5:25:5:2 or about 30:10:23:5:25:5:2. In some implementations, the soft chew formulation further includes: citric acid anhydrous; potassium sorbate; and DL-α-tocopheryl acetate.

In a further aspect, the invention also relates to a starch-free soft chew for oral delivery of at least one active ingredient to an animal. The soft chew includes a starch-free soft chew formulation, such as one described above, and at least one active ingredient. In some implementations, the soft chew formulation is made without adding water as an excipient.

In certain implementations of the soft chew, the at least one active ingredient includes an active pharmaceutical ingredient, such as an antiparasitic (e.g., anthelmintic). Exemplary active pharmaceutical ingredients suitable for the soft chew include, without limitation, milbemycin oxime, ivermectin, moxidectin, abamectin, selamectin, pyrantel (e.g., pyrantel pamoate), febantel, fenbendazole, oxibendazole, emodepside, piperazine, mebendazole, levamisole, praziquantel, and oxantel. In certain exemplary implementations, the active pharmaceutical ingredient is milbemycin oxime, praziquantel, ivermectin, or pyrantel. In some implementations, the at least one active ingredient further includes a second active pharmaceutical ingredient, such as an antiparasitic (e.g., anthelmintic). In some implementations of the soft chew, the at least one active ingredient includes: milbemycin oxime or ivermectin; and praziquantel or pyrantel. For example, in some implementations, the at least one active ingredient includes milbemycin oxime and praziquantel. In some implementations, the at least one active ingredient includes ivermectin and pyrantel.

In some implementations of the soft chew, the at least one active ingredient is moisture-sensitive. By way of example, the at least one active ingredient can include, in certain implementations, a moisture-sensitive active pharmaceutical ingredient, such as clavulanic acid, nitenpyram, milbemycin oxime, or ivermectin.

In some implementations of the soft chew, the at least one active ingredient includes a cannabinoid (e.g., a phytocannabinoid or a synthetic cannabinoid). Exemplary cannabinoids for use in the soft chew include, without limitation, tetrahydrocannabinol, cannabidiol, cannabinol, cannabichromene, cannabigerol, 2-arachidonoylglycerol, and anandamide.

In some implementations of the soft chew, the at least one active ingredient includes an active nutritional ingredient. Exemplary active nutritional ingredients for use in the soft chew include, without limitation, glucosamine, enzymes, fish oils, herbal ingredients, and the like.

In one exemplary implementation of the soft chew, the soft chew formulation includes: 15-90% w/w dibasic calcium phosphate dihydrate; 5-30% w/w flavoring; 5-40% w/w microcrystalline cellulose; 0-15% w/w croscarmellose sodium; 0-5% w/w sodium stearyl fumarate or magnesium stearate; 15-50% w/w glycerin; 15-50% w/w medium-chain triglycerides; 0-5% w/w citric acid anhydrous; 0.01-3% w/w potassium sorbate; and 0.01-3% w/w DL-α-tocopheryl acetate. In another exemplary implementation of the soft chew, the soft chew formulation includes: 10-60% w/w dibasic calcium phosphate dihydrate; 5-35% w/w flavoring; 5-40% w/w microcrystalline cellulose; 0-15% w/w croscarmellose sodium; 0-5% w/w sodium stearyl fumarate or magnesium stearate; 15-50% w/w glycerin; 2-20% w/w medium-chain triglycerides; 0-5% w/w citric acid anhydrous; 0.01-3% w/w potassium sorbate; and 0.01-3% w/w DL-α-tocopheryl acetate.

In another aspect, the invention relates to a composition of starch-free, non-water excipients for use in the final dosage form of a soft chew for oral administration of at least one active ingredient to an animal. The composition consists essentially of non-starch solid excipients and non-water liquid excipients, and the starch-free, non-water excipients include: dibasic calcium phosphate (e.g., hydrous dibasic calcium phosphate, such as dibasic calcium phosphate dihydrate); microcrystalline cellulose; glycerin; and triglycerides of fatty acids with carbon chain lengths of C6-C12. In one implementation, the weight ratio of dibasic calcium phosphate to microcrystalline cellulose is about 1:1 to about 4:1 (e.g., about 2:1 to about 3:1).

Exemplary triglycerides of fatty acids suitable for use in the composition include, without limitation, caprylic triglycerides, capric triglycerides, and a mixture thereof. In certain implementations, the triglycerides of fatty acids are medium chain triglycerides. In some implementations, the weight ratio of glycerin to the triglycerides of fatty acids is about 4:1 to 7:1 (e.g., about 5:1 to 6:1).

In some implementations of the composition, the starch-free, non-water excipients further include at least one of: a filler, such as lactose (e.g., lactose monohydrate) and the like; a flavoring agent; a disintegrant, such as croscarmellose sodium and the like; a lubricant, such as magnesium stearate, stearic acid, sodium stearyl fumarate, and the like; a preservative, such as citric acid, potassium sorbate, and the like; an antioxidant, such as citric acid (e.g., citric acid anhydrous), α-tocopherol (e.g., DL-α-tocopheryl acetate), and the like; and a binder, such as povidone (e.g., povidone K30), and the like.

Exemplary active ingredients for use in the composition include, without limitation, active pharmaceutical ingredients and active nutritional ingredients. By way of example, the at least one active ingredient can include an active pharmaceutical ingredient, such as an antiparasitic (e.g., an anthelmintic), a cannabinoid, and the like. In certain implementations, the at least one active ingredient includes an active nutritional ingredient.

In a further aspect, the invention relates to a process for making a starch-free soft chew for oral delivery of at least one active ingredient to an animal, by: (a) dry-mixing at least two non-starch dry excipients in a mixer (e.g., a low-shear mixer or a high-shear mixer); and (b) mixing the dry excipients into a dough-like material by adding into the mixer at least two non-water liquid excipients (e.g., by adding into the mixer the at least two non-water liquid excipients in a sequential manner). In certain implementations, the process includes at least one of the following additional steps: (c) forming the dough-like material into ribbon; (d) portioning the ribbon into soft chew portions (e.g., using a portioning tool); and (e) packaging the soft chew portions. In some implementations, the process also includes the step of dry-mixing the at least one active ingredient with the starch-free dry excipients. In some implementations, the process is carried out under ambient room-temperature conditions.

In some implementations of the process, the at least two non-water liquid excipients include a humectant (e.g., glycerin) and a solvent (e.g., medium chain triglycerides). By way of example, and without limitation, the humectant can be added into the mixer first and the solvent can be added into the mixer thereafter.

In some implementations, the process also includes the step of mixing the at least one active ingredient with one of the non-water liquid excipients. By way of example, and without limitation, the at least one active ingredient can be mixed with the solvent.

The details of one or more implementations are set forth in the description below. Other features and advantages will be apparent from the specification and the claims.

BRIEF DESCRIPTION OF DRAWINGS

Features and advantages of embodiments of the present application will become apparent from the following detailed description and the appended drawings, in which.

DETAILED DESCRIPTION

Figure 1:
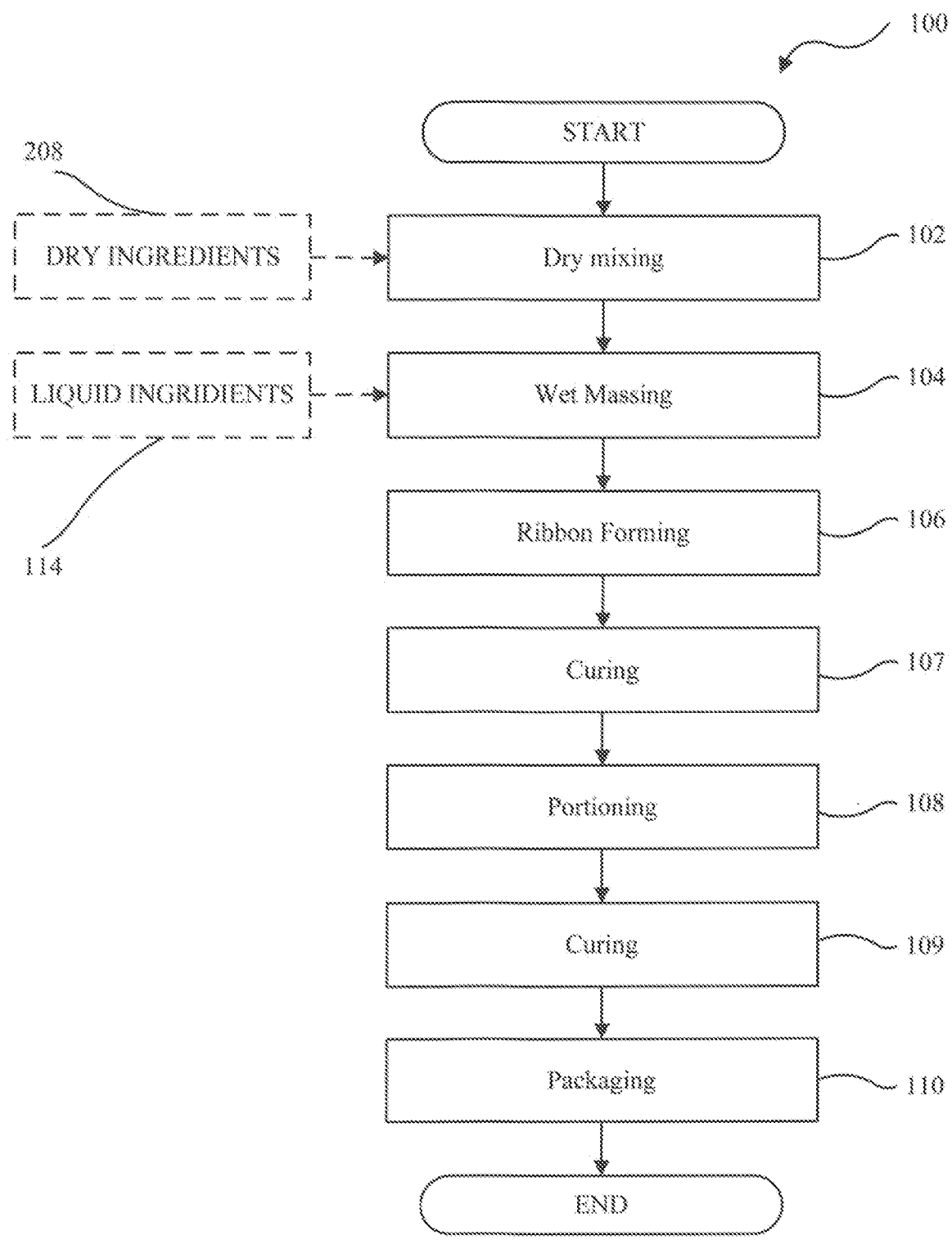
FIG. 1 is a simplified flowchart diagram illustrating a manufacturing process exemplary of an embodiment of the present invention, that is used to prepare a soft chew.

The present invention discloses a composition or dosage form suitable for oral delivery of one or more pharmaceutically-active ingredients and other medicaments, including nutraceuticals, that is particularly well suited for treating companion animals such as dogs, cats, or other pets. More specifically, the inventors describe herein a soft chew as the final dosage form of a veterinary drug or nutritional ingredient and a formulation of excipients for such a soft chew. Embodiments of the soft chew can enhance the stability and bioavailability of a pharmaceutically-active ingredient contained therein, can exhibit structural integrity to hold a sufficient amount of flavoring, and/or can retain over time a soft and malleable texture. Embodiments of the soft chew can also suppress microbial growth and exhibit improved shelf-life. In addition, embodiments of the soft chew formulations described herein can perform well in dynamic dissolution tests of drug products.

The main chemical reactions that affect the stability of a drug are generally considered to be oxidation and hydrolysis. Oxidation involves the removal of electrons from a molecule (or the addition of oxygen); the oxidation reaction can be initiated by light, heat, or certain trace metals. Oxidative degradation can often be reduced to acceptable levels by storing susceptible drugs in the absence of light and oxygen, or by using antioxidants in the formulation.

Hydrolysis is the reaction of a molecule with water, resulting in the cleavage of a chemical bond within that molecule. Hydrolysis is the more common pathway for drug breakdown and is particularly problematic in formulations for veterinary applications in which the dosage forms to be swallowed (e.g., tablets or capsules) are not preferred. Unfortunately, many active pharmaceutical ingredients are moisture-sensitive because they contain functional groups that are susceptible to hydrolysis. Examples of such moisture-sensitive drugs are nitenpyram, milbemycin oxime, clavulanic acid, and ivermectin. In particular, ivermectin is highly sensitive to an aqueous environment and subject to degradation; therefore, it must be protected from moisture. Its chemical instability on contact with water is well-emphasized in U.S. 2016/0303151A1.

Water content in a pharmaceutical product can be quantified by way of Karl Fischer titration. It is generally understood that the water content of a product includes bound and unbound water. In addition to measuring the total amount of water by the Karl Fischer method, measuring the level of water activity or unbound water can be an effective method for evaluating the effects of water on safety and stability of a product. The level of water activity may also affect the textural properties of soft chew products. While low water activity is desired for safety and stability, it may lead to undesirable textural attributes, such as hardness, dryness, staleness, and toughness, especially in conventional soft chews containing starch.

In embodiments of the soft chew described herein, in which starch and water are not used as excipients, water exists mostly as bound water. The level of free or unbound water in the soft chew is effectively low. Therefore, the water content of the soft chew remains generally consistent, without significant fluctuation, over time.

The composition of excipients described by the inventors supports the stability and bioavailability of the dosage form. Furthermore, a soft chew made in accordance with the present invention can be more easily designed into many different shapes and sizes, taking the appearance of a treat rather than a medicated pill.

Advantageously, the disclosed composition of functional ingredients produces a texture that remains soft and malleable over time. This allows in-vitro dissolution methods of discriminating nature to be used as a reliable quality control test.

A discriminating dissolution method is a method that is able to differentiate drug products manufactured under target conditions from drug products that are intentionally manufactured with meaningful variations. The expression "meaningful variations" is used to represent changes in the formulation, raw material attributes, and/or process parameters that may occur during manufacturing of the drug product. Ideally, the discriminating method should be able to detect changes to the formulation, raw material attributes, and processing conditions (i.e., batch-to-batch variations or planned deviations). Hence, the dissolution test should be able to indicate possible changes in the quality of the product before in-vivo performance is affected. One such change can be an increase in the hardness of a soft-chew formulation over time. The requisite dissolution method should be discriminating enough to detect the change.

The availability of a discriminatory dissolution method for use in either quality control testing or product evaluation in quality-by-design trials is necessary for products intended for markets in developed countries. Major regulatory agencies expect discriminatory dissolution methods for the quality control of pharmaceutical products, especially oral solid dosage forms.

Many pharmaceutical soft chews currently on the market contain starch as an excipient. These products generally do not have desirable physicochemical attributes. They tend to have high moisture content and a hard texture and exhibit slow disintegration and dissolution. These undesirable physicochemical properties may be due to the presence of starch in the formulation. Starch is an excipient with high moisture content which can easily absorb moisture in high-humidity environments and lose moisture when exposed to a dry environment. The fluctuations in moisture within the chew can change its texture over time. These changes in the properties of soft chews can, in turn, affect the bioavailability of the products.

The soft chews described herein do not require starch or added water as excipients. They can exhibit stable water content and water activity at low levels, and maintain malleability in texture over time, thereby permitting measurement of release of active pharmaceutical ingredients using discriminatory dissolution methods and generation of dissolution profiles of the soft chews.

Embodiments of the present invention can be advantageous over the prior art for various reasons. For example:

Embodiments of the soft chew formulations can exhibit high stability and bioavailability and eliminate the need to add starch and/or water.

In certain embodiments of the soft chew formulations, water activity (i.e., amount of free-water) is sufficiently low. A low level of free water content is important in a drug delivery system because many active pharmaceutical ingredients are moisture-sensitive.

Embodiments of the soft chew formulations can achieve an adequate shelf-life by reducing the chance of microbial growth.

The avoidance of starch leads to higher-quality soft chews by providing a more uniform surface appearance and generally improved look and also improving digestion by companion animals like dogs and cats which lack essential enzymes for digesting starch.

Embodiments of the soft chew formulations can be more easily designed into many different shapes and sizes, appearing like treats rather than pills.

Embodiments of the soft chew formulations can maintain a soft and malleable texture over time.

Embodiments of the soft chew formulations can allow in-vitro dissolution methods of discriminating nature to be used as a reliable quality-control test.

In certain embodiments, the entire process of preparing a soft chew can be carried out under ambient room-temperature conditions, which is particularly beneficial for heat-sensitive active ingredients.

Easy scale-up of manufacturing is facilitated by producing consistent-quality soft chew products across largely different batch sizes.

Exemplary Embodiments

In one aspect, the invention relates to a starch-free soft chew that includes one or more pharmaceutically- or nutritionally-active ingredients and a plurality of excipients (e.g., pharmaceutical-grade excipients). The soft chew contains no added water and the plurality of excipients contain no starch. Exemplary starch-free excipients for use in the soft chew can include a filler, a flavoring agent or palatant, a humectant, a solvent, a softening agent, a preservative, an antioxidant, and a lubricant. In one implementation, the plurality of excipients include at least two dry or solid ingredients and at least two wet or liquid ingredients. The solid ingredients do not include starch as an excipient and the liquid ingredients do not include water as an excipient. In one exemplary implementation, the solid ingredients at least include dibasic calcium phosphate (e.g., anhydrous, monohydrous, or dihydrous) and microcrystalline cellulose, the liquid ingredients at least include glycerin and medium chain triglycerides, the soft chew contains no added water, and the filler contains no starch. In some implementations, the plurality of excipients further includes at least one flavoring agent.

In accordance with another aspect, the invention relates to a process for making a soft chew. The process includes some or all of the following steps: dry-mixing a plurality of dry or solid ingredients in a mixer; wet-mixing with a plurality of wet or liquid ingredients to a dough-like material; forming the dough-like material into ribbon; portioning the ribbon into a predetermined length of soft chew portions; and packaging the soft chew portions. The dry ingredients do not include starch as an excipient and the liquid ingredients do not include water as an excipient.

In another aspect, the invention relates to a soft chew that includes at least one active ingredient and a plurality of excipients. The active ingredient may be a pharmaceutical or nutritional agent that can be orally administered. The plurality of excipients are a combination of non-starch solid excipients and non-water liquid excipients. In some implementations, the soft chew includes two active ingredients which may be pharmaceutical or nutritional. In other implementations, the soft chew includes more than two active ingredients which may be pharmaceutical or nutritional. In further implementations, the multiple active ingredients are either all pharmaceutical ingredients or all nutritional ingredients.

In certain implementations, the soft chew described herein includes at least one active ingredient which is an anti-parasitic agent. Anti-parasitic agents may be ether ecto-parasiticidal or endo-parasiticidal, or both. In some implementations, the soft chew contains no added water, the active ingredient is an ecto-parasiticidal agent which belongs to a class of isoxazoline, and the plurality of excipients contains no starch. Exemplary ecto-parasiticidal agents of the isoxazoline class include, for example, afoxolaner, fluralaner, sarolaner, lotilaner, and the like. In other implementations, the soft chew contains no added water, the active ingredient is an endo-parasiticidal or anthelmintic agent which belongs to a class of macrocyclic lactone, and the plurality of excipients contains no starch. Exemplary anthelmintic agents of the macrocyclic-lactone class include, for example, milbemycin oxime, moxidectin, ivermectin, abamectin, doramectin, eprinomectin, selamectin, and the like.

In certain implementations, the soft chew contains two or more active ingredients; at least one is ecto-parasiticidal and at least one is endo-parasiticidal. In some implementations, the active ingredients are a combination of the isoxazoline and macrocyclic-lactone classes. In other implementations, the soft chew contains an active pharmaceutical ingredient which belongs to a class of chemicals excluding isoxazoline.

In one implementation, the plurality of excipients in the soft chew includes a filler, a flavoring agent, a humectant, a solvent, a softening agent, a preservative, an antioxidant, and a lubricant. Exemplary fillers include, without limitation, dibasic calcium phosphate dihydrate (DiCal or DCPD), microcrystalline cellulose, lactose, and any combination of any of the foregoing. In one exemplary implementation, the filler is dicalcium phosphate dihydrate, microcrystalline cellulose, or a combination of any of the foregoing. Exemplary solvents include, without limitation, caprylic/capric triglycerides, medium chain triglycerides, long-chain triglycerides, and any combination of any of the foregoing. In one exemplary implementation, the solvent is medium chain triglycerides or a mixture of caprylic and capric triglycerides. Exemplary softening agents include, without limitation, magnesium stearate, stearic acid, sodium stearyl fumarate, and any combination of any of the foregoing.

The plurality of excipients can further include a binder and/or disintegrant and/or surfactant. Exemplary binders include, without limitation, povidone, hydroxyl propyl cellulose (HPC), hydroxyl methyl cellulose (HPMC), and any combination of any of the foregoing.

In one exemplary implementation, the soft chew includes at least one active pharmaceutical ingredient and the following excipients: 10-90% w/w dicalcium phosphate dihydrate; 5-35% w/w flavoring; 5-40% w/w microcrystalline cellulose; 0-15% w/w croscarmellose sodium; 0-5% w/w sodium stearyl fumarate or magnesium stearate; 15-50% w/w glycerin; 2-50% w/w medium chain triglycerides; 0-5% w/w citric acid anhydrous; 0.01-3% w/w potassium sorbate; and 0.01-3% w/w DL-α-tocopheryl acetate. In another exemplary implementation, the soft chew includes at least one active pharmaceutical ingredient and the following excipients: 15-90% w/w dicalcium phosphate dihydrate; 5-30% w/w flavoring; 5-40% w/w microcrystalline cellulose; 0-15% w/w croscarmellose sodium; 0-5% w/w sodium stearyl fumarate or magnesium stearate; 15-50% w/w glycerin; 15-50% w/w medium chain triglycerides; 0-5% w/w citric acid anhydrous; 0.01-3% w/w potassium sorbate; and 0.01-3% w/w DL-α-tocopheryl acetate. In a further exemplary implementation, the soft chew includes at least one active pharmaceutical ingredient and the following excipients: 10-60% w/w dicalcium phosphate dihydrate; 5-35% w/w flavoring; 5-40% w/w microcrystalline cellulose; 0-15% w/w croscarmellose sodium; 0-5% w/w sodium stearyl fumarate or magnesium stearate; 15-50% w/w glycerin; 2-20% w/w medium chain triglycerides; 0-5% w/w citric acid anhydrous; 0.01-3% w/w potassium sorbate; and 0.01-3% w/w DL-α-tocopheryl acetate.

In another aspect, the invention relates to a process for making a soft chew by: (a) dry-mixing a plurality of dry or solid ingredients, in a mixer (e.g., a low-shear mixer or a high-shear mixer); and (b) wet-mixing by adding a plurality of wet or liquid ingredients into the mixer into a dough-like material. The process can include one or more of the following additional steps: (c) forming the dough-like material into ribbon; (d) portioning the ribbon into a predetermined length of soft chew portions (e.g., using a portioning tool); and (e) packaging the soft chew portions. In one preferred embodiment, the wet-mixing step includes the following substeps: adding a humectant into the mixer, mixing the blend in the mixer, and then adding a solvent into the mixer. In one implementation, the entire process is carried out under room-temperature conditions without the need for heating or cooling.

In one implementation of the process, the plurality of dry ingredients includes at least one active ingredient that is a pharmaceutical or nutritional agent. In another implementation of the process, the plurality of liquid ingredients includes at least one active ingredient that is a pharmaceutical or nutritional agent. In yet another implementation of the process, an active ingredient in a powder form is mixed with, or dissolved in, a liquid excipient and then added into the mixer. In further implementations of the process, the plurality of dry ingredients include at least one of a filler, a flavoring agent, a humectant, a solvent, a softening agent, a preservative, an antioxidant, and a lubricant, and the plurality of liquid ingredients include at least one of a filler, a flavoring agent, a humectant, a solvent, a softening agent, a preservative, an antioxidant, and a lubricant.

In accordance with another aspect of the present invention, there is provided a starch-free composition of excipients for a final dosage in the form of a soft chew that does not necessitate the use of starch or added water. In one implementation, the starch-free composition of excipients includes at least two solid ingredients and at least two liquid ingredients. In exemplary implementations, the solid ingredients do not include starch as an excipient and the liquid ingredients do not include water as an excipient. In some implementations, the starch-free composition of excipients is a vehicle for oral administration of at least one active ingredient that is moisture-sensitive. In some implementations, all excipients are pharmaceutical-grade.

In yet another implementation, the solid ingredients at least include dibasic calcium phosphate and microcrystalline cellulose, and the liquid ingredients at least include glycerin and triglycerides of fatty acids with carbon-chain lengths of C6-C12, wherein no starch or added water is required. In some implementations, the starch-free composition of excipients is a vehicle for oral administration of at least one active ingredient that is moisture-sensitive. In yet another implementation, the starch-free composition of excipients further includes at least one flavoring agent. In still yet another implementation, all excipients are pharmaceutical-grade.

The dibasic calcium phosphate can be hydrous or anhydrous. In certain implementations, dibasic calcium phosphate hydrous, and, more preferably, dibasic calcium phosphate dihydrate, is used.

The triglycerides of fatty acids with carbon-chain length of C6-C12 can be triglycerides of any one of C6-C12 fatty acids or any combination thereof. In certain implementations, caprylic/capric triglycerides or medium chain triglycerides, and, more preferably, medium chain triglycerides, are used.

By way of example, and without limitation, an exemplary starch-free formulation of excipients for use in a soft chew as described herein includes dibasic calcium phosphate dihydrate and microcrystalline at the weight ratio of about 1:1 to 4:1 (e.g., about 2:1 to 3:1 or about 2.5:1 to 3:1). Glycerin and medium chain triglycerides can be included at the weight ratio of about 2:1 to 7:1 (e.g., about 4:1 to 7:1 or about 5:1 to 6:1).

As is well known, many active pharmaceutical ingredients (APIs) used to treat both humans and non-human animals are unpalatable and are unsuited for oral delivery unless accompanied by appropriate excipients. The starch-free formulation of excipients described herein can further include flavoring. Exemplary implementations of the composition and dosage form described herein can contain a flavoring agent in an amount sufficient to mask the unpalatable taste of an API while, at the same time, inducing voluntary acceptance by an animal, so that there may be no need to force the animal to take the medicament or to involve a veterinarian.

By way of example, the flavoring can be included at the weight ratio of about 0.1 to 0.35 (e.g., about 0.15 to 0.3 or about 0.2 to 0.25) based on the total weight of all excipients. The flavoring agents are preferably pharmaceutical grade. Exemplary flavoring agents include, but are not limited to, FlavorPal™ (TetraGenX, Saint Laurent, Quebec, Canada), Desiccated Pork Liver Powder™ (Gurvey and Berry, Toronto, Ontario, Canada), Provesta® 356 (Ohly Inc., Hamburg, Germany), Provesta® 400 (Ohly Inc., Hamburg, Germany), and PC-0125 Artificial Powdered Beef Flavor™ (Pet Flavors Inc., Melbourne, Fla., USA). A soft chew of the present invention that includes FlavorPal™ can show excellent voluntary acceptance by an animal, thereby enhancing the animal's perception that the soft chew is a treat rather than a medication.

In one implementation, the composition of excipients for use in a soft chew includes dibasic calcium phosphate dihydrate, microcrystalline cellulose, glycerin, and medium chain triglycerides, but does not include either starch or water as an excipient. This starch-free composition can provide the final dosage form of a soft chew with sufficient structural integrity, desired softness and malleability, low water activity, and consistent water content. The starch-free carrier composition can further include at least one flavoring agent. An antioxidant (e.g., DL-α-tocopheryl acetate) can also be added to the composition.

The starch-free carrier composition can be especially suitable for formulating a moisture-sensitive active ingredient. Excipients such as dicalcium phosphate dihydrate, microcrystalline cellulose, glycerin, and medium chain triglycerides generally show good compatibility with most active pharmaceutical ingredients known in the market.

Formulation of Excipients

Embodiments of the present invention include formulation of excipients for a final dosage in the form of a soft chew. A soft chew is used to refer to material that is not brittle or crunchy, so that it would not immediately break apart when chewed by a companion animal or a pet.

Filler/Bulking Agent

In accordance with one exemplary embodiment of the present invention, the soft chew formulation includes a filler or bulking agent. Exemplary compounds that may be used as a filler or bulking agent include dibasic calcium phosphate hydrous or anhydrous, microcrystalline cellulose (MCC), lactose hydrous or anhydrous, or combinations thereof. Preferably, dibasic calcium phosphate dihydrate (DiCal or DCPD), microcrystalline cellulose (MCC), lactose monohydrate, or any combination of any of the foregoing can be used as fillers. However, starch is not used in fillers used in embodiments of the present invention.

Although starch is often used as an excipient primarily in many conventional oral solid-dosage formulations, it is avoided as filler in exemplary embodiments of the present invention. Starch has a chemical formula $(C_6H_{10}O_5)_n$ where n=300-1000. Many conventional fillers include and even often prefer the use of starch which may be pre-gelatinized starch or non-pregelatinized starch. Further, the use of extrusion often induces starch gelatinization depending on the particular filler or bulking agent used and the presence of other input ingredients that contain starch.

Despite the common use of starch in the conventional soft-chew formulations, starch has certain detrimental effects on the final dosage form of a soft chew containing an API. For example, starch has a high moisture content, which promotes water activity in the dosage form. High water activity in turn leads to decreased stability of an API (e.g., hydrolysis) and increased microbial activity, thereby compromising the efficacy of the API and the shelf-life of the soft chew. In addition, companion animals like dogs and cats cannot easily digest starch. These animals are carnivores with short simple digestive tracts and lack essential enzymes such as amylase needed for digestion of starch. Therefore, the starch-free formulation of the present invention is more beneficial for these animals.

Embodiments of the present invention do not use or require starch. Neither pre-gelatinized starch nor non-pre-gelatinized starch is required for use as a filler ingredient in embodiments of the present invention. Advantageously, the avoidance of starch in the filler leads to higher quality soft chews. At least some of the soft chews, exemplary of embodiments of the present invention, have been shown to have a more uniform surface appearance and generally improved look. In addition, starch has a high moisture content and by not using starch, at least some embodiments of the present invention, will have much lower moisture content which can accommodate moisture-sensitive APIs.

Instead, embodiments of the present invention use dibasic calcium phosphate, MCC, lactose, or combinations of these as filler or bulking agent. Accordingly, some embodiments of the present invention may use a filler that includes dibasic calcium phosphate. Other embodiments of the present invention may thus use a filler that includes MCC and yet other embodiments of the present invention may thus use a filler that includes lactose. Some embodiments may use a filler that includes both MCC and dibasic calcium phosphate, while other embodiments may use a filler that includes both MCC and lactose, while some other embodiments may use a filler that includes both lactose and dibasic calcium phosphate. Yet other embodiments may use a filler that includes all of MCC, dibasic calcium phosphate, and lactose. Exemplary lactoses include, without limitation, lactose hydrous, lactose anhydrous, and lactose monohydrate.

Microcrystalline cellulose is widely used as a diluent and binder in pharmaceutical formulations and is generally considered a relatively nontoxic and nonirritant material. As a pharmaceutical excipient, MCC has been shown to be well tolerated with a variety of APIs. Microcrystalline cellulose is a purified, partially depolymerized cellulose that occurs as a white, odorless and tasteless crystalline powder, made up of porous particles. Microcrystalline cellulose is commercially available in several different grades. These MCCs differ in their method of manufacture, particle size, moisture, flow and other physical properties. In exemplary embodiments, MCCs may comprise about 5% to 40% by weight ("w/w") of the soft chew.

Dibasic calcium phosphate is available in an anhydrous or hydrous form. Its dihydrate has chemical formula $CaHPO_4 \cdot 2H_2O$ and is widely used as a diluent in tablet formulations as well as a source of calcium and phosphorous in nutritional supplements. As a pharmaceutical excipient, dibasic calcium phosphate dihydrate has been shown to be well tolerated with a variety of APIs. Since DiCal is abrasive, a lubricant is generally used when utilized in a pharmaceutical dosage form and is usually a requirement for tableting. Dibasic calcium phosphate dihydrate is nonhygroscopic and stable at temperatures close to room temperature. In other exemplary embodiments, dibasic calcium phosphate dihydrate may comprise 15% to 90% by weight ("w/w") of the soft chew. DCPD can support the structural integrity of a soft chew of the present invention through synergistic interaction with MCC.

Flavor

Many flavoring agents may be used in compositions exemplary of an embodiment of the present the invention to improve the palatability of the dosage. Meat or beef flavorings used in exemplary embodiments may be naturally derived or artificially formulated to have a meat or beef flavor.

Natural flavorings are often made up of dried and pulverized or powdered meat which may be obtained from domesticated meat animals including cattle such as cows or bulls, pigs, deer, sheep, goats, poultry which may include turkey, chicken, duck and the like.

Non-animal, often plant derived flavorings, are also known in the art and may be used in embodiments of the present invention. These may include peanuts, fruits, sweeteners, honey, sugar, maple syrup and fructose, parsley, celery, peppermint, spearmint, garlic, and the like. In exemplary embodiments, the favoring or palatant may comprise 5% to 30% w/w the soft chew.

Preferably, the flavoring agent is pharmaceutical-grade. Exemplary flavoring agents include, without limitation, FlavorPal™, Desiccated Pork Liver Powder™, Provesta® 356, Provesta® 400, and PC-0125 Artificial Powdered Beef Flavor™.

Softener/Humectant

At least some embodiments of the present invention utilize glycerol as a softener or humectant. Glycerol is a clear, colorless, viscous organic compound having the molecular formula $HOCH_2CHOHCH_2OH$.

Humectants are known in the art, and many conventional soft chews have been known to use ammonium alginate, sodium lactate, sorbitol, triacetin, xylitol, and glycerin. In preferred embodiments of the present invention, glycerol is used as the softener or humectant. Glycerol is also known to be bacteriostatic and bactericidal against certain bacterial species.

Water (Non-Use of)

In contrast to many known and conventional formulations and processes, embodiments of the present invention do not introduce water in the soft chew composition. Soft chews are typically manufactured by blending a mixture of ingredients and using an extruder.

The importance of controlling water activity or free-water content in an oral delivery system is emphasized in U.S. Pat. No. 6,387,381. The free or available water in a soft chew promotes microbial growth and participates in and supports chemical and enzymatic reactions and spoilage processes, especially in the presence of flavoring agents with nutrients. This amount of free water is known as water activity, and it is more important for chemical and microbial stability of a final product than total water content.

In conventional soft chew manufacturing, water introduced into the mixture must generally be of pharmaceutical grade. No water is used as an excipient in embodiments of the soft chews described herein; the absence of water as excipient avoids the need for use of costly pharmaceutical-grade water, and reduces the likelihood of microbial growth or lost potency by the active ingredient. The fact that neither water nor starch which has a high moisture content is added to the formulation makes embodiments of the present invention capable of accommodating moisture-sensitive APIs.

Advantageously, processes and costs associated with maintaining water of a pharmaceutical grade are avoided in embodiments of the present invention, as water is not introduced into the mixture in the manufacturing process.

This contrasts sharply with some of the chews known in the art, such as the aforementioned U.S. Pat. No. 8,541,019 which discloses a palatable ductile chewable veterinary composition which includes up to 9% water.

Solvents/Other Liquids

Some embodiments of the present invention use solvents including caprylic/capric triglyceride or medium chain triglyceride (MCT), as well as vegetable oils termed long-chain triglycerides (LCT). In exemplary embodiments, MCT may comprise 15% to 50% w/w the soft chew. In other embodiments, the solvent can be triglycerides of fatty acids with carbon-chain lengths of C6-C12, including triglycerides of any one of C6-C12 fatty acids, triglycerides of any combination of C6-C12 fatty acids, caprylic/capric triglycerides, and medium chain triglycerides (MCTs).

Triglycerides of medium-chain length fatty acids, known as medium-chain triglycerides or MCTs, can be synthesized by esterifying glycerol with fatty acids of carbon chain lengths of C8 or C10. MCTs are usually commercially-available as a mixture of glycerol esters of C8 (octanoic acid or caprylic acid) and C10 (decanoic acid or capric acid) fatty acids, with small amounts (<1% of each) of glycerol esters of C6 (hexanoic acid or caproic acid) and C12 (dodecanoic acid or lauric acid) fatty acids as disclosed in WO2013126990A1.

MCTs have different physical characteristics from those of ordinary animal fats or vegetable oils, including lower viscosities and higher solubility in alcohol. While fatty acids found in MCTs are saturated like animal fats, MCTs are liquid at room temperature, like vegetable oils. WO 2013/126990A1 indicates that MCTs may, when used as an excipient, improve the solubilisation of active ingredient having poor water solubility. It is also noted that MCTs are generally known to be antimicrobial and antiviral.

MCT is a multi-functional excipient and, as noted below, can function as a lubricant. MCTs can increase processability of soft-chew formulations during extruding, ribbon-forming, and the like, and can facilitate high-speed processing.

Softening Agents

Embodiments of the present invention also use softening agents. Softening agents are utilized to decrease hardness of the soft chew product by usually limiting the density.

Pharmaceutically acceptable softening agents are well known and may include for example polysaccharides, vegetable or animal fat, such as cocoa butter, seed oil, palm oil or coconut oil, or alcohols such as glycerin. In exemplary embodiments, glycerin may comprise 15% to 50% w/w the soft chew.

In preferred embodiments of the present invention, the softening agents used are magnesium stearate (MgSt), stearic acid which has a chemical formula $C_{17}H_{35}CO_2H$ and/or sodium stearyl fumarate ($C_{22}H_{39}NaO_4$) which is also used as a lubricant.

Binders

Exemplary embodiments of the soft chew may include a binder in the form of povidone, hydroxyl propyl cellulose (HPC), hydroxyl methyl cellulose (HPMC), or combinations thereof. The use of a binder is optional in some embodiments of the present invention.

Povidone has a chemical formula $(C_6H_9NO)_n$ with a molecular weight in the range 2500-3000000. Povidone may also act as a disintegrant, dissolution aid, and a suspending agent in addition to it uses as a binder. Povidone products are often accompanied by K numbers, which are indicative of the viscosity in solution and also the mean molecular weights of the specific povidones (e.g., povidone K30).

In some embodiments, the binder, when present, may include just povidone while in other embodiments, the binder may include just HPC; and in yet other embodiments, the binder may include just HPMC. In some embodiments, the binder, when present, may include just povidone and HPC while in other embodiments the binder may include just povidone and HPMC; and in yet other embodiments, the binder may include just HPC and HPMC. In some exemplary embodiments the soft chew may include all three of povidone, hydroxyl propyl cellulose (HPC), and hydroxyl methyl cellulose (HPMC).

Surfactants

Exemplary embodiments of the soft chew may include surfactants. Surfactants are as surface-active agents sometimes also called wetting agents, emulsifying agents or suspending agents depending on their properties and use. Surfactants lower the surface tension or interfacial tension between two liquids or between a liquid and a solid. They are soluble in both organic solvents and water and are suitable for ingestion. However, the use of a surfactant is optional in embodiments of the present invention.

Disintegrants

Exemplary embodiments of the soft chew may include a disintegrant. In exemplary embodiments, the disintegrate may comprise up to 15% w/w the soft chew. Exemplary disintegrants known in the art include crospovidone, croscarmellose sodium, and cellulose. As noted above, povidone may also function as a disintegrant. The use of a disintegrant is optional in some embodiments of the present invention. In specific exemplary embodiments, croscarmellose sodium may comprise up to 15% w/w the soft chew. Disintegrants are also used to modify texture and can be used to modify drug release.

Antioxidants

Exemplary embodiments of the soft chew may include an antioxidant. Examples of antioxidants include, alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene), and monothioglycerol. In exemplary embodiments, the antioxidant may comprise 0.01-3% w/w the soft chew.

Other antioxidants may also include tocopherols such as alpha, beta, or delta-tocopherol, tocopherol esters, alpha-tocopherol acetate; alkyl gallates, butylated hydroxyanisole, butylated hydroxytoluene, citric acid anhydrous and hydrous, edetic acid and its salts, lecithin and tartaric acid. Other antioxidants are resveratrol, quercetin, benzoic acid, dimethyl thiourea (DMTU), hesperetin, tetrahydrocurcumin, tetrahydrodemethoxycurcumin, and monothioglycerol. In specific embodiments, alpha tocopherol or DL-α-tocopheryl acetate may comprise 0.01-3% w/w the soft chew.

Preservatives

Exemplary embodiments of the soft chew may include a preservative. Examples of preservatives include well-known preservative excipients that are pharmaceutically acceptable such as benzoic acid, ascorbic acid, calcium propionate, potassium sorbate, citric acid hydrous and anhydrous, and the like. In exemplary embodiments, potassium sorbate may comprise 0.01-3% w/w the soft chew and citric acid anhydrous may comprise up to 5% w/w the soft chew.

In some cases, some of the antioxidants noted above may also play the same role as a preservative.

Lubricants

Exemplary embodiments of the soft chew may include a lubricant. Examples of lubricants include caprylic/capric triglyceride or medium chain triglyceride (MCT), as well as vegetable oils termed long-chain triglycerides (LCT), magnesium stearate (MgSt), stearic acid, sodium stearyl fumarate, and combinations thereof. In exemplary embodiments, the lubricants such as sodium stearyl fumarate may comprise up to 5% w/w the soft chew. Medium chain triglycerides (MCT) may comprise up to 15-50% w/w the soft chew.

Lubricants such as LCT, MCT and MgSt, stearic acid, and sodium stearyl fumarate help lubricate the machine for easier processing. The lubricant formulation also lubricates equipment especially during ribbon forming. Additionally, the lubricants may also help mitigate potentially abrasive characteristics other excipients such as DiCal.

Active Ingredients

The above ingredients or excipients described in connection with exemplary embodiments of a soft chew can, of course, be used in conjunction with one or more suitable active ingredients, including active pharmaceutical ingredients (APIs) and active nutritional ingredients.

Active pharmaceutical ingredients are the biologically-active components of drug products and include substances, such as cannabinoids, which may be legally controlled and regulated more strictly than other pharmaceutical ingredients. Active nutritional ingredients are active ingredients found in nutraceuticals.

Active ingredients suitable for use in the soft chews described herein can be any drugs, nutraceutical agents, or the like which can be orally administered. Examples include, without limitation, anti-infective agents such as antibiotics, antibacterials, antifungals, antiprotozoans, and antivirals; analgesics; anti-parasitics such as ecto-parasiticides and endo-parasiticides (anthelmintics); hormones and derivatives thereof; anti-inflammatories such as non-steroidal anti-inflammatories, steroids, and the like; cannabinoids, including plant cannabinoids (phytocannabinoids) and synthetic cannabinoids; behavior modifiers; vaccines; antacids; laxatives; anticonvulsants; sedatives; tranquilizers; antitussives; antihistamines; decongestants; expectorants; appetite stimulants and suppressants; minerals and vitamins; amino acids; fatty acids; glucosamine; enzymes; fish oils; herbal ingredients; and traditional medicines.

Among veterinary drugs, anti-parasitic and anti-infective drugs have played a major role in the market for veterinary medicinal products, with their combined share reaching almost 50%. Anti-infectives encompass, in particular, antibiotics, antifungals, and antivirals. Exemplary antibiotics for use in the soft chews described herein include, without limitation, amoxicillin, cefalexin, clavulanic acid, enrofloxacin, and metronidazole. Anti-parasitics encompass antiparasitic agents against external parasites present on the body surfaces (ecto-parasiticides) and anti-parasitic agents against internal parasites present inside the body (endo-parasiticides). Exemplary ecto-parasiticides for use in the soft chews described herein include, without limitation: (a) isoxazoline compounds such as afoxolaner, fluralaner, sarolaner, and lotilaner; and (b) neonicotinoid compounds such as imidacloprid, acetamiprid, thiacloprid, dinotefuran, nitenpyram, thiamethoxam, and clothianidin. Exemplary endo-parasiticides (anthelmintics) for use in the soft chews described herein include, without limitation: (a) macrocyclic lactones such as avermectins (e.g., ivermectin, abamectin, doramectin, eprinomectin, selamectin) and milbemycins (e.g., milbemycin oxime, moxidectin); and (b) other anthelmintics such as pyrantel, febantel, fenbendazole, oxibendazole, emodepside, piperazine, mebendazole, levamisole, praziquantel, and oxantel. An anti-infective or anti-parasitic API may be included in a soft chew alone or in combination with one or more other active ingredients.

Many APIs are moisture-sensitive. Exemplary moisture-sensitive active ingredients are clavulanic acid, nitenpyram, milbemycin oxime, and ivermectin. These compounds may become unstable upon contact with water and an aqueous environment should be avoided during the process of preparing the soft chew and also in the soft chew formulation itself.

In certain embodiments, the APIs exclude the isoxazoline class of compounds. In other embodiments, the APIs do not exclude the isoxazoline class of compounds. Any active pharmaceutical ingredients that may be used to treat companion animals may be included as APIs in embodiments of the present invention.

Methods of Manufacture

Processes or methods exemplary of embodiments of the present invention, for soft chews, will now be described. A process, exemplary of an embodiment of the present invention, for the manufacture of soft chews involves mixing dry ingredients to form mixture of homogeneous consistency. Liquid ingredients are added and wet-massing of the wet mixture is performed, or the blend is mixed, until a dough-like consistency is obtained. Suitable machinery is then used to form ribbons of suitable length and shape from the wet mass which are then portioned into desired formulation lengths having the final dose weight. These are then packaged into a suitable package for presentation, storage and/or shipping.

FIG. 1 illustrates the steps involved in one exemplary manufacturing method or process 100 used to make the soft chew. As illustrated, process 100 starts with dry ingredients 208 that are to be mixed together in a mixer. The mixer may be a low-shear mixer or a high-shear mixer. A low-shear mixer is preferred for certain embodiments.

Preprocessing steps to prepare the dry ingredients 208 for use will be described later with reference to FIG. 2. At step 102, the dry ingredients 208 are added into a mixer and mixed together.

The dry-mixing step 102 in FIG. 1, is carried out until a homogenous consistency of the dry mixture is obtained. Liquid ingredients 114 are then added to the mixer and the mixing is continued in wet-massing or wet-mixing step 104. Here, glycerin may be added followed by the addition of MCT. Wet-massing or wet-mixing step 104 continues until a wet mass of desired dough-like consistency is achieved.

A ribbon-forming step 106 involving the use of a ribbon-forming machine or an extruder to form the wet mass into ribbons of suitable processing length and shape, as defined by machine equipment die tooling, is carried out next. Advantageously, the formulation of ingredients in the earlier steps provides lubrication to the equipment used, particularly during ribbon-forming step 106.

At step 107 the ribbon that resulted from the ribbon-forming step 106 is cured. In some embodiments, the curing step 107 may take up to 24 hours. In step 108 the ribbons formed in the previous ribbon-forming step 106 are portioned into desired formulation lengths to obtain the final dose weight as a function of the dimensions and product density.

At step 109 the portions resulting from step 108 are cured. In some embodiments, the curing of the portions in step 109 may take up to 72 hours. The portions are then packaged in step 110 into desired packaging presentations.

Figure 2:
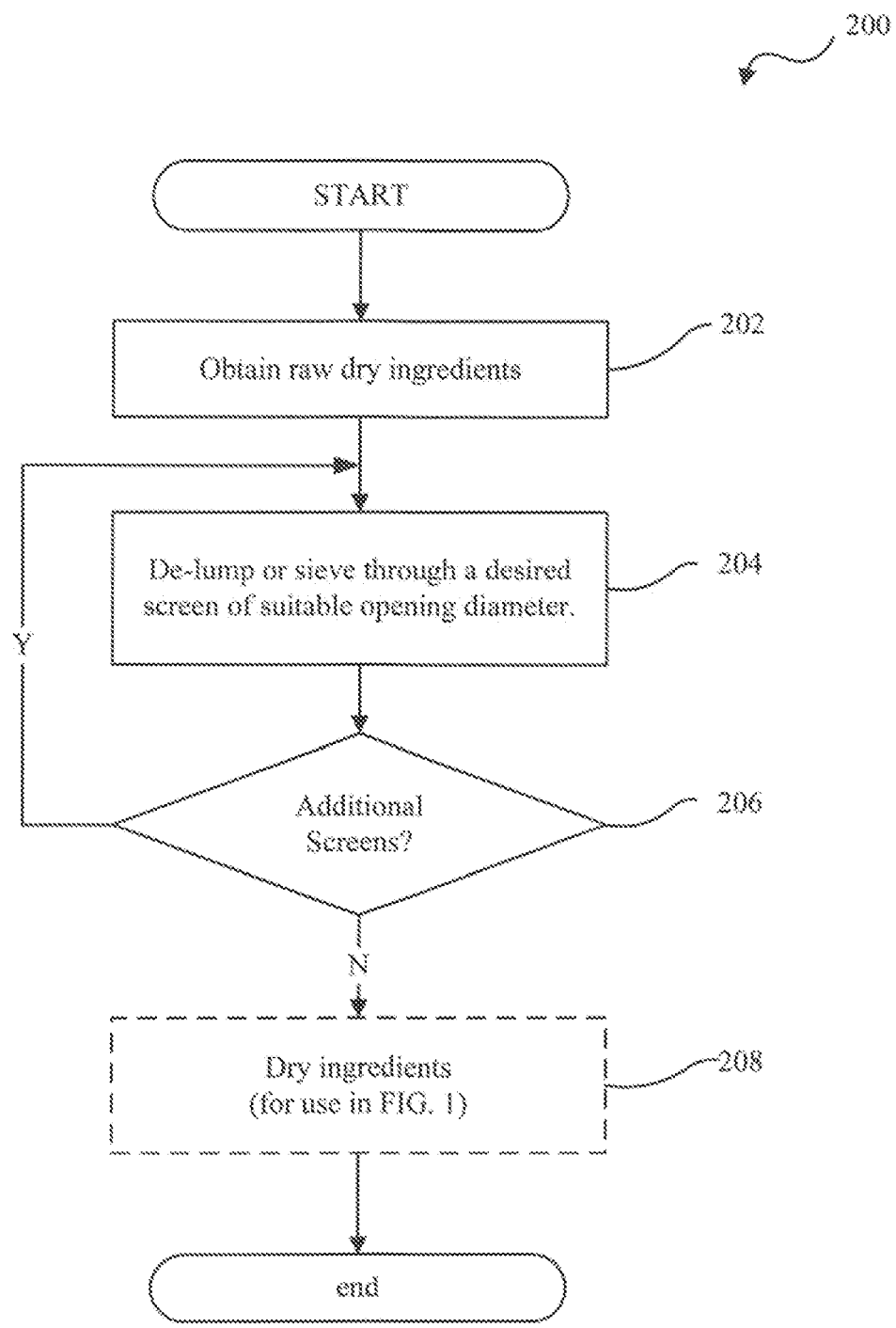
FIG. 2 is a simplified flowchart diagram illustrating process steps involved in preparing dry ingredients for use in the manufacturing process of FIG. 1.

FIG. 2 is a simplified flowchart diagram illustrating process steps involved in preparing dry ingredients for use in the manufacturing process 100 as described above. The preparation process 200 starts with obtaining raw dry ingredients in step 202 which are de-clumped or sieved though a desired screen of suitable opening diameter in step 204 or through combination of multiple screens as needed in steps 206, 204. Suitable dry ingredients 208 are then achieved which can fed into the mixer in FIG. 1 for the dry mixing step 102.

Some of the excipients discussed above may be provided as part of the dry ingredients 208 while other excipients may be provided as part of the liquid ingredients 114.

Figure 3:
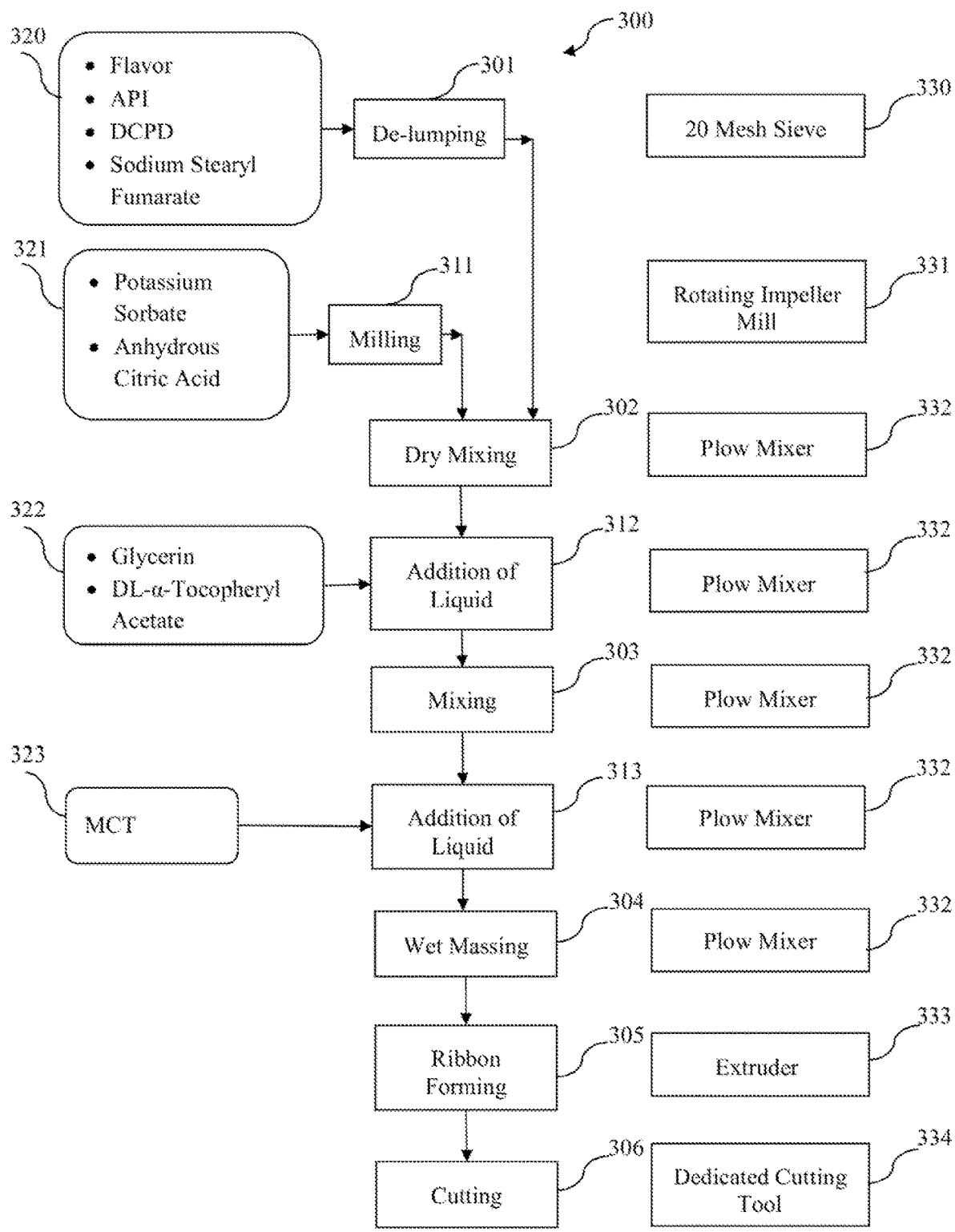
FIG. 3 is a simplified flowchart diagram illustrating an exemplary manufacturing process used to prepare an embodiment of a soft chew described herein.

FIG. 3 illustrates the steps involved in an exemplary manufacturing method or process 300 used to make an embodiment of a soft chew disclosed herein.

Process 300 starts with preparation of the dry ingredients. At the step of de-lumping 301, dry ingredients 320 such as a flavoring agent, an API, a filler (e.g., DCPD), and a lubricant (e.g., magnesium stearate, sodium stearyl fumarate, or a combination of any of the foregoing) are de-clumped or sieved through a 20 mesh screen 330. At the step of milling 311, preservatives 321, such as potassium sorbate and anhydrous citric acid, are milled through a rotating impeller mill 331. The de-lumped dry ingredients 320 and the milled ingredients 321 are then loaded into a plow mixer 332, along with the rest of the dry ingredients, for example, a second filler (e.g., microcrystalline cellulose) and a disintegrant (e.g., croscarmellose sodium) which may not require preparation prior to mixing. At the step of dry-mixing 302, the dry ingredients are mixed in the plow mixer 332 operating at about 100 rpm for about 2 minutes.

The liquid ingredients can be prepared prior to mixing with the dry ingredients. If the soft chew formulation incorporates a second API that requires accurate dosing due to its high potency, the second API can be first dissolved in a solvent 323 such as MCT oil to prepare an overage solution of the second API and solvent. A propeller mixer and appropriately-sized vessel can be used for the purpose. In addition, a humectant (e.g., glycerin) and an antioxidant (e.g., DL-α-tocopheryl acetate) 322 can be manually mixed together using a spatula for about 1 minute.

Liquid is added at step 312 with the plow mixer 332 operating at about 100 rpm in which the glycerin/DL-α-tocopheryl acetate mixture 322 is added to the mixing blend for a period of time of about 2 minutes. After the entire quantity of glycerin/DL-α-tocopheryl acetate 322 is added, mixing step 303 is performed by mixing the blend in the plow mixer 332 for about 1 additional minute. Addition of liquid is carried out at step 313 with the plow mixer 332 operating at about 100 rpm in which the solvent 323, such as MCT, or the overage solution of the second API and solvent is then added to the mixture for the period of time of about 2 minutes.

For the wet-massing step 304, the plow mixer 332 is opened and visually inspected for residues stuck to the wall and the plows of the mixer. The residues can be scraped from the wall and plows of the mixer and returned to the center of the mixer. Wet-massing step 304 is carried out by mixing the blend at room temperature until the material achieves a dough-like consistency, such as for approximately 17 minutes.

For the step of ribbon forming 305, the wet mass from the wet-massing step 304 was discharged from the plow mixer 332 and loaded into the hopper of a ribbon-forming machine or an extruder 333. Ribbons with an appropriate length (e.g., about 15") are formed at room temperature and placed on parchment lined trays. The ribbons were cured at room temperature for 18-24 hours. Then, at the step of cutting 306, the ribbons are cut into segments of a predetermined unit weight using a dedicated tool 334 to provide the final dose weight of the API(s). The portions are then cured at room temperature for a period of time, such as for 72 hours, prior to bulk packaging.

Processes exemplary of embodiments of the present invention can be carried out under ambient room-temperature conditions without requiring any specific heating or cooling. This is particularly beneficial for heat-sensitive active ingredients.

Processes exemplary of embodiments of the present invention may involve the addition of one or more pharmaceutically-active ingredients and a set of excipients including at least one of a filler, a flavoring agent, a humectant, a solvent, a softening agent, a preservative, an antioxidant and a lubricant. Optionally a binder, disintegrant and surfactant may also be added into the mix of ingredients.

An active ingredient in powder form can be mixed with other dry or solid ingredient(s) including dry excipient(s) while an active ingredient in liquid form can be mixed with other liquid ingredient(s) including liquid excipient(s) prior to the wet-massing step. For example, an active ingredient such as milbemycin oxime, praziquantel, or pyrantel pamoate can be evenly mixed with dry excipients such as potassium sorbate, citric acid, flavoring agent, croscarmellose sodium, microcrystalline cellulose, magnesium stearate, and sodium stearyl fumarate. In some embodiments, an active ingredient in powder form can be processed together with one or more dry excipients to produce an intermediate mixture before being added to and mixed with other dry ingredients. The dry excipient(s) that can be used to form the intermediate mixture may include a filler (e.g., lactose) and/or a binder (e.g., povidone). For example, milbemycin oxime can be processed with lactose monohydrate and povidone K30 to form an intermediate mixture before being blended into other dry ingredients.

In certain embodiments, an active ingredient in powder form can be mixed with liquid excipient(s) to facilitate accurate dosing of the active ingredient. For example, ivermectin is exceptionally potent, with effective dosages levels that are unusually low (in micrograms); therefore, accurate measurement of ivermectin is critical during the process of making an ivermectin-containing soft chew. Although ivermectin is normally provided in powder form, it can be more beneficial to prepare and use an overage solution of ivermectin in a solvent such as caprylic/capric triglycerides or medium chain triglycerides.

In some embodiments, the plurality of dry ingredients may include at least one of: a filler, a flavoring agent, a humectant, a solvent, a softening agent, a preservative, an antioxidant, and a lubricant.

In some embodiments, the plurality of liquid ingredients may include at least one of: a filler, a flavoring agent, a humectant, a solvent, a softening agent, a preservative, an antioxidant, and a lubricant.

As noted earlier, embodiments of the present invention have several advantages including the manufacture of soft chews with textures that remain soft and malleable over time. Further, some embodiments of the soft chews exemplary of the present invention, allow in-vitro dissolution methods of discriminating nature to be used as a reliable quality control test.

The application may be better understood by reference to the following non-limiting examples, which are provided as exemplary embodiments of the invention. The following examples, which are set forth to aid in an understanding of the invention, should not be construed to limit in any way the scope of the invention as defined in the claims which follow thereafter.

EXAMPLES

Example 1—Preparation of Soft Chew A

Milbemycin Oxime/Praziquantel (5.75 mg/57 mg) Soft Chews

TABLE 1

| Composition of Soft Chew A | | | |
|---|---|---|---|
| Ingredients | % (w/w) | mg/chew | Batch Size (g) |
| Milbemycin Oxime | 0.23 | 5.75 | 2.3 |
| Praziquantel | 2.28 | 57.00 | 22.8 |
| Lactose Monohydrate | 3.275 | 81.875 | 32.75 |
| Povidone K30 | 0.0355 | 0.8875 | 0.355 |
| Dibasic Calcium Phosphate Dihydrate (DCPD) | 24.585 | 614.625 | 245.85 |
| Microcrystalline Cellulose (MCC) | 9.66 | 241.5 | 96.6 |
| Flavoring agent | 20.0 | 500.00 | 200.0 |
| Croscarmellose Sodium | 4.5 | 112.50 | 45.0 |
| Glycerin | 28.0 | 700.00 | 280.0 |
| Medium chain Triglyceride (MCT) | 4.575 | 114.375 | 45.75 |
| Magnesium stearate | 2.000 | 50.00 | 20.0 |
| Citric Acid Anhydrous | 0.5 | 12.50 | 5.0 |
| Potassium Sorbate | 0.3 | 7.50 | 3.0 |
| DL-α-Tocopheryl Acetate | 0.05 | 1.25 | 0.5 |
| TOTAL | 100.0 | 2500 | 1000.0 |

The excipients used as listed above were pharmaceutical-grade and met USP standards.

DL-α-tocopheryl acetate was added to the MCT oil and mixed manually with a spatula. The dry ingredients, milbemycin oxime/povidone K30/lactose monohydrate intermediate (previously prepared), praziquantel, DCPD, potassium sorbate (previously grounded using a mortar), citric acid anhydrous, flavoring agent, croscarmellose sodium, MCC, and magnesium stearate, were tumble-blended together and then de-clumped or sieved though a 20 mesh screen. The de-lumped dry ingredients were tumble-blended again for 2 minutes and then loaded into a low-shear mixer. While operating the mixer, glycerin was added to the blend (time of addition=2 minutes). After the entire quantity of glycerin was added, the blend was mixed for 1 additional minute. Then, the MCT oil/DL-α-tocopheryl acetate solution was added to the mixture (time of addition=2 minutes). The blend was mixed at room temperature until the material achieved a dough-like consistency (approximately 9 minutes). The wet mass was then moved to a ribbon-forming machine. Ribbons with diameter of 11 mm and length of about 25 cm were formed at room temperature. The ribbons were cured at room temperature for 24 hours. Then, the ribbons were portioned into 2.5 g±0.13 g segments to provide the final dose weight of milbemycin oxime (5.75 mg) and praziquantel (57 mg). The portions were then cured at room temperature for 72 hours prior to bulk packaging.

The whole process above was carried out under ambient room-temperature conditions without heating or cooling required.

Example 2—Dissolution Profile of Soft Chew A

Milbemycin Oxime/Praziquantel (5.75 mg/57 mg) Soft Chews

TABLE 2

Dissolution Profile of Soft Chew A

| Time (min) | Time 0 | | 6 Months | |
|---|---|---|---|---|
| | Milbemycin Oxime (% Dissolved) | Praziquantel (% Dissolved) | Milbemycin Oxime (% Dissolved) | Praziquantel (% Dissolved) |
| 5 | 19 | 24 | 28 | 34 |
| 10 | 41 | 46 | 54 | 60 |
| 20 | 73 | 78 | 83 | 89 |
| 30 | 89 | 95 | 91 | 97 |
| 45 | 92 | 99 | 92 | 97 |
| 60 | 93 | 100 | 93 | 97 |
| 75 | 91 | 98 | 93 | 97 |
| 90 | 94 | 99 | 94 | 97 |
| 120 | 94 | 99 | 93 | 97 |

Dissolution Conditions: 0.5% SLS (sodium lauryl sulfate) in water, Volume 1000 ml, 75 rpm, 37.0° C. ± 0.5° C.

Figure 4:
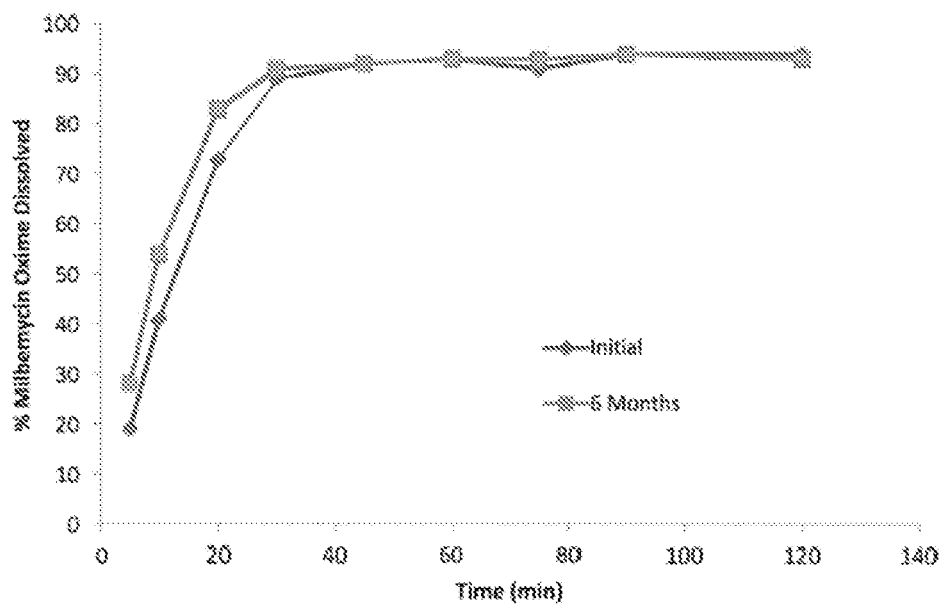
FIG. 4 is a plot showing the average dissolution of milbemycin oxime from 2.5 g portions of Soft Chew A of Example 1, which were stored at 25° C. and 60% relative humidity (RH) for 6 months.
Figure 5:
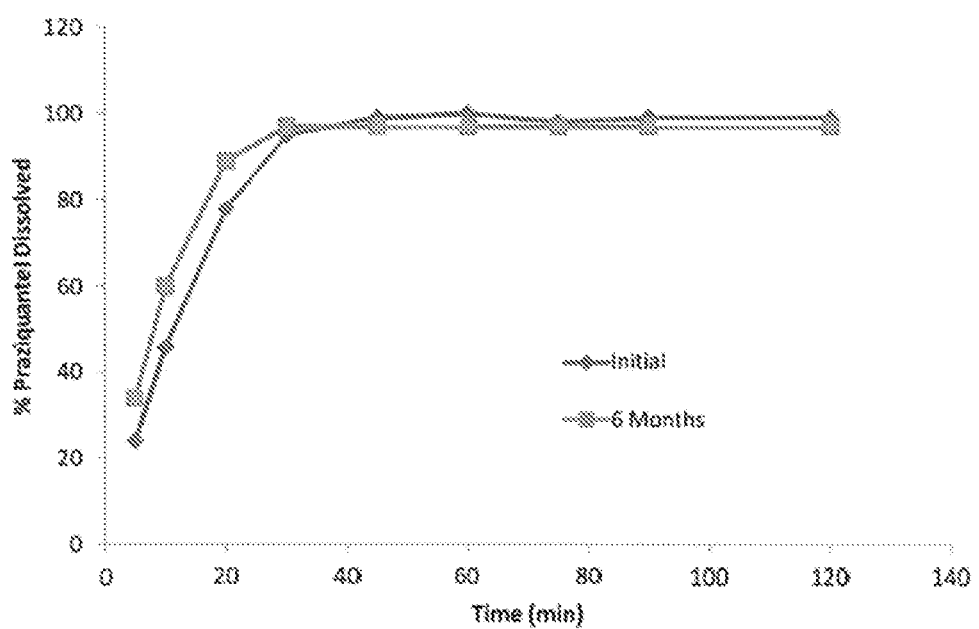
FIG. 5 is a plot showing the average dissolution of praziquantel from 2.5 g portions of Soft Chew A of Example 1, which were stored at 25° C. and 60% relative humidity (RH) for 6 months.

The soft chews of Example 1 (Soft Chew A, 2.5 g per chew) were stored at 25° C. and 60% relative humidity (RH) for 6 months. Dissolution tests were carried out under the conditions indicated above for each API (milbemycin oxime and praziquantel) at time-points of zero and 6 months. Samples were withdrawn at various time intervals to generate a dissolution profile at each given time-point. The resulting dissolution profiles for milbemycin oxime and praziquantel are shown in Table 2 above and also in FIGS. 4 and 5, respectively. The dissolution profiles of each API remained rapid and consistent with no significant changes after the 6-month time-period.

Example 3—Stability of Soft Chew A

Milbemycin Oxime/Praziquantel (5.75 mg/57 mg) Soft Chews

TABLE 3

Stability of Soft Chew A

| Test Method | Time 0 | 1 Month | 2 Months | 3 Months | 6 Months |
|---|---|---|---|---|---|
| Moisture - Karl Fischer | N/A | 5.5 | N/A | 3.8 | 5.5 |
| Milbemycin Oxime Assay - HPLC | 95.1 | 95.4 | 92.9 | 93.7 | 94.9 |
| Praziquantel Assay - HPLC | 99.9 | 98.7 | 98.0 | 98.9 | 97.5 |

The drug product was packaged in 150 cc HDPE (high-density polyethylene) bottles containing 20 soft chews each and stored in 25° C./60% RH conditions. The soft chews were tested for moisture content, milbemycin oxime, and praziquantel assay over 6 months. As shown in Table 3, all of the test results remained stable over time.

Example 4—Physical Attributes of Soft Chew A Over Time

Milbemycin Oxime/Praziquantel (5.75 mg/57 mg) Soft Chews

TABLE 4

Physical Attributes of Soft Chew A over Time

| Day | Disintegration Time (min:sec) | Texture* (N) |
|---|---|---|
| 0 | 19:00 | 1.83 |
| 1 | 19:10 | 3.40 |
| 7 | 20:58 | 3.49 |
| 14 | 13:11 | 3.25 |
| 28 | 13:34 | 3.65 |

*Texture is measured as the peak force (in Newton) necessary to push a sphere of 5.0 mm in diameter to a depth of 2.0 mm into the soft chew with a velocity of 1.0 mm/sec.

The soft chews were allowed to cure at ambient conditions over a period of 28 days. The disintegration and texture of the soft chews was measured on day 0, day 1, day 7, and day 28 after manufacture. As shown in Table 4, the drug product retained its fast disintegration time and the soft chew remained soft and malleable over time.

Example 5—Preparation of Soft Chew B

Ivermectin/Pyrantel (68 µg/57 mg) Soft Chews

TABLE 5

Composition of Soft Chew B

| Ingredients | % (w/w) | mg/chew | Batch Size (g) |
|---|---|---|---|
| Ivermectin | 0.00272 | 0.068 mg (68 µg) | 0.0272 |
| Pyrantel Pamoate | 6.572 | 164.3 (57 mg Pyrantel) | 65.72 (22.8 g Pyrantel) |
| DCPD | 29.0 | 725.0 | 290.0 |
| MCC | 10.0 | 250.0 | 100.0 |

TABLE 5-continued

Composition of Soft Chew B

| Ingredients | % (w/w) | mg/chew | Batch Size (g) |
|---|---|---|---|
| Flavoring agent | 20.0 | 500.0 | 200.0 |
| Croscarmellose Sodium | 1.5 | 37.5 | 15.0 |
| Glycerin | 26.0 | 650.0 | 260.0 |
| MCT | 4.575 | 114.375 | 45.75 |
| Sodium Stearyl Fumarate | 1.5 | 37.5 | 15.0 |
| Citric Acid Anhydrous | 0.5 | 12.5 | 5.0 |
| Potassium Sorbate | 0.3 | 7.5 | 3.0 |
| DL-α-Tocopheryl Acetate | 0.05 | 1.25 | 0.5 |
| TOTAL | 100.0 | 2500.0 | 1000.0 |

The excipients used as listed above were pharmaceutical-grade and met USP standards.

Ivermectin was first dissolved in MCT oil using a propeller mixer and appropriately sized vessel. An extra 10% ivermectin and MCT oil was weighed out in order to prepare a 10% ivermectin/MCT oil overage solution. The dry ingredients, pyrantel pamoate, DCPD, potassium sorbate (previously grounded using a mortar), citric acid, flavoring agent, croscarmellose sodium, microcrystalline cellulose and sodium stearyl fumarate, were de-clumped or sieved though a 20-mesh screen. The de-lumped dry ingredients were tumble blended for 2 minutes and then loaded into the mixing bowl of a planetary mixer. DL-α-tocopheryl acetate was added to the vessel containing glycerin and manually mixed with a spatula. While operating the mixer, the glycerin/DL-α-tocopheryl acetate emulsion was added to the blend (time of addition=2 minutes). After the entire quantity of glycerin/DL-α-tocopheryl acetate was added, the blend was mixed for 1 additional minute. The precise amount of ivermectin/MCT oil solution was added to the mixture (time of addition=2 minutes). The blend was mixed at room temperature until the material achieved a dough-like consistency (approximately 50 minutes). The wet mass was then moved to a ribbon forming machine. Ribbons with diameter of 11 mm and length of about 25 cm were formed at room temperature. The ribbons were cured at room temperature for 24 hours. Then, the ribbons were portioned into 2.5 g±0.13 g segments to provide the final dose weight of ivermectin (68 µg) and pyrantel (57 mg). The portions were then cured at room temperature for 72 hours prior to bulk packaging.

The whole process above was carried out under ambient room-temperature conditions without heating or cooling required.

Example 6—Dissolution Profile of Soft Chew B

Ivermectin/Pyrantel (68 µg/57 mg) Soft Chews

TABLE 6

Dissolution Profile of Soft Chew B

| | Time 0 | | 4 Weeks | |
|---|---|---|---|---|
| Time (min) | Ivermectin (% dissolved) | Pyrantel (% dissolved) | Ivermectin (% dissolved) | Pyrantel (% dissolved) |
| 10 | 15 | 15 | 16 | 15 |
| 20 | 32 | 31 | 31 | 30 |
| 30 | 40 | 41 | 41 | 40 |
| 45 | 50 | 51 | 49 | 48 |
| 60 | 55 | 56 | 57 | 54 |
| 90 | 70 | 71 | 72 | 69 |
| 120 | 81 | 82 | 85 | 80 |
| 180 | 92 | 94 | 96 | 91 |

Dissolution Conditions: 4% SLS in water, Volume 500 ml, 75 rpm, 37.0° C. ± 0.5° C.

The soft chews of Example 5 (Soft Chew B, 2.5 g per chew) were stored at 25° C. and 60% relative humidity (RH) for 4 weeks. The dissolution tests were carried out under the conditions indicated above for each API (ivermectin and pyrantel) at time-points of zero and 4 weeks. Samples were withdrawn at various time intervals to generate a dissolution profile at each given time-point. As shown in Table 6 above, the dissolution profiles of each API remained fast and consistent with no significant changes after the 4-week time-period.

Example 7—Stability of Soft Chew B

Ivermectin/Pyrantel (68 µg/57 mg) Soft Chews

TABLE 7

Stability of Soft Chew B

| Test Method | Time 0 | 1 Month | 2 Months | 3 Months | 6 Months |
|---|---|---|---|---|---|
| Moisture - Karl Fischer | 2.3 | 2.9 | 3.5 | 4.0 | 3.4 |
| Ivermectin Assay - HPLC | 101.1 | 101.5 | 100.7 | 96.3 | 94.0 |
| Pyrantel Assay - HPLC | 100.9 | 100.9 | 102.2 | 100.2 | 100.9 |

The drug product was packaged in 60 cc HDPE bottles containing 15 soft chews each and stored in 25° C./60% RH conditions. The soft chews were tested for moisture content, ivermectin and pyrantel assay over 6 months. As shown in Table 7, all of the test results remained stable over time.

Example 8—Physical Attributes of Soft Chew B Over Time

Ivermectin/Pyrantel (68 µg/57 mg) Soft Chews

TABLE 8

Physical Attributes of Soft Chew B over Time

| Day | Disintegration Time (min:sec) | Texture* (N) |
|---|---|---|
| 0 | 48:50 | 2.65 |
| 1 | 25:41 | 9.08 |
| 7 | 29:42 | 7.06 |
| 14 | 34:00 | 6.18 |
| 28 | 33:26 | 6.81 |

*Texture is measured as the peak force (in Newton) necessary to push a sphere of 5.0 mm in diameter to a depth of 2.0 mm into the soft chew with a velocity of 1.0 mm/sec.

The soft chews were allowed to cure at ambient conditions over a period of 28 days. The disintegration and texture of the soft chews was measured on day 0, day 1, day 7, and day 28 after manufacture. As shown in Table 8, the drug product retained its fast disintegration time and the soft chew remained soft and malleable over time.

Example 9—Preparation of Soft Chew C

Ivermectin/Pyrantel (68 μg/57 mg) Soft Chews

TABLE 9

Composition of Soft Chew C

| Ingredients | % (w/w) | mg/chew | Batch Size (g) |
|---|---|---|---|
| Ivermectin | 0.00272 | 0.068 mg (68 μg) | 1.360 |
| Pyrantel Pamoate | 6.572 | 164.3 (57 mg Pyrantel) | 3,286.0 |
| DCPD | 29.0 | 725.0 | 14,500.0 |
| MCC | 10.0 | 250.0 | 5,000.0 |
| Flavoring agent | 20.0 | 500.0 | 10,000.0 |
| Croscarmellose Sodium | 1.5 | 37.5 | 750.0 |
| Glycerin | 26.0 | 650.0 | 13,000.0 |
| MCT | 4.575 | 114.375 | 2287.5 |
| Sodium Stearyl Fumarate | 1.5 | 37.5 | 750.0 |
| Anhydrous Citric Acid | 0.5 | 12.5 | 250.0 |
| Potassium Sorbate | 0.3 | 7.5 | 150.0 |
| DL-α-Tocopheryl Acetate | 0.05 | 1.25 | 25.0 |
| TOTAL | 100 | 2500 | 50,000 |

The excipients used as listed above were pharmaceutical-grade and met USP standards.

Ivermectin was first dissolved in MCT oil using a propeller mixer and appropriately sized vessel. An extra 10% ivermectin and MCT oil was weighed out in order to prepare a 10% ivermectin/MCT oil overage solution. Potassium sorbate and anhydrous citric acid were milled through a rotating impeller mill (Comil®—Quadro Engineering Corp., Waterloo, Ontario, Canada) equipped with a 2A024R screen. The dry ingredients, flavoring agent, pyrantel pamoate, DCPD, and sodium stearyl fumarate, were de-clumped or sieved though a 20-mesh screen. The milled potassium sorbate and anhydrous citric acid, the de-lumped dry ingredients, microcrystalline cellulose, and croscarmellose sodium were loaded into a plow mixer and mixed for 2 minutes at 100 rpm. The DL-α-tocopheryl acetate was added to the vessel containing glycerin and manually mixed with a spatula for 1 minute. With the plow mixer operating at 100 rpm, the glycerin/DL-α-tocopheryl acetate mixture was added to the mixing blend (time of addition=2 minutes). After the entire quantity of glycerin/DL-α-tocopheryl acetate was added, the blend was mixed for 1 additional minute. With the plow mixer operating at 100 rpm, the precise amount of ivermectin/MCT oil solution was added to the mixture (time of addition=2 minutes). The plow mixer was opened and visually inspected for residues stuck to the wall and the plows of the mixer. The residues were scraped from the wall and plows of the mixer and returned to the center of the mixer. The blend was mixed at room temperature until the material achieved a dough-like consistency (approximately 17 minutes). The wet mass was discharged from the plow mixer and loaded into the hopper of a ribbon-forming machine (Vemag Robot 500™ portioner—VEMAG Maschinenbau GmbH, Verden, Germany). Ribbons with length of about 15" were formed at room temperature and placed on parchment lined trays. The ribbons were cured at room temperature for 18-24 hours. Then the ribbons were cut into 2.5 g±0.125 g segments using a dedicated tool to provide the final dose weight of ivermectin (68 μg) and pyrantel (57 mg). The portions were then cured at room temperature for 72 hours (3 days) prior to bulk packaging.

The whole process above was carried out under ambient room-temperature conditions without heating or cooling required. In addition, the batch size was significantly increased (i.e., 50 times) from the batch size used for the same formulation in Example 5.

Example 10—Dissolution Profile of Soft Chew C

Ivermectin/Pyrantel (68 μg/57 mg) Soft Chews

TABLE 10

Dissolution Profile of Soft Chew C

| Time (min) | Day 3 | | Day 3 + 2 Weeks | | Day 3 + 4 Weeks | |
|---|---|---|---|---|---|---|
| | Ivermectin (% dissolved) | Pyrantel (% dissolved) | Ivermectin (% dissolved) | Pyrantel (% dissolved) | Ivermectin (% dissolved) | Pyrantel (% dissolved) |
| 10 | 20 | 15 | 12 | 14 | 26 | 25 |
| 20 | 33 | 28 | 22 | 24 | 43 | 45 |
| 30 | 43 | 39 | 27 | 29 | 55 | 56 |
| 45 | 52 | 50 | 32 | 34 | 67 | 67 |
| 60 | 59 | 57 | 38 | 40 | 72 | 75 |
| 90 | 69 | 69 | 59 | 60 | 85 | 90 |
| 120 | 77 | 81 | 77 | 80 | 91 | 97 |
| 180 | 89 | 93 | 92 | 96 | 93 | 100 |

Dissolution Conditions: 4% SLS in water, Volume 500 ml, 75 rpm, 37.0° C. ± 0.5° C.

The soft chews of Example 9 (Soft Chew C, 2.5 g per chew) were stored at 25° C. and 60% relative humidity (RH) for 4 weeks. The dissolution tests were carried out under the conditions indicated above for each API (ivermectin and pyrantel) at time-points of Day 3, Day 3+2 weeks, and Day 3+4 weeks. Samples were withdrawn at various time intervals to generate a dissolution profile at each given time-point. As shown in Table 6 above, the dissolution profiles of each API remained fast and consistent with no major changes after the 4-week time-period.

Example 12—Physical Attributes of Soft Chew C Over Time

Ivermectin/Pyrantel (68 µg/57 mg) Soft Chews

TABLE 12

Physical Attributes of Soft Chew C over Time

| Day | Texture* (N) |
|---|---|
| 3 | 7.5 |
| 3 + 2 weeks | 11 |
| 3 + 4 weeks | 11 |

*Texture is measured as the peak force (in Newtons) necessary to push a sphere of ¼ inch diameter to a depth of 2.0 mm into the soft chew with a velocity of 1.0 mm/sec.

The soft chews were allowed to cure at ambient conditions over a period of 4 weeks. The texture of the soft chews was measured on day 3, day 3+2 weeks, and day 3+4 weeks after manufacture. As shown in Table 12, the drug product remained soft and malleable over time.

Example 13—Preparation of Soft Chew D

Ivermectin/Pyrantel (136 µg/114 mg) Soft Chews

TABLE 13

Composition of Soft Chew D

| Ingredients | % (w/w) | mg/chew | Batch Size (g) |
|---|---|---|---|
| Ivermectin | 0.00272 | 0.136 mg (136 µg) | 1.360 |
| Pyrantel Pamoate | 6.572 | 328.6 (114 mg Pyrantel) | 3,286.0 |
| DCPD | 29.0 | 1450.0 | 14,500.0 |
| MCC | 10.0 | 500.0 | 5,000.0 |
| Flavoring agent | 20.0 | 1000.0 | 10,000.0 |
| Croscarmellose Sodium | 1.5 | 75.0 | 750.0 |
| Glycerin | 26.0 | 1300.0 | 13,000.0 |
| MCT | 4.575 | 228.75 | 2287.5 |
| Sodium Stearyl Fumarate | 1.5 | 75.0 | 750.0 |
| Anhydrous Citric Acid | 0.5 | 25.0 | 250.0 |
| Potassium Sorbate | 0.3 | 15.0 | 150.0 |
| DL-α-Tocopheryl Acetate | 0.05 | 2.5 | 25.0 |
| TOTAL | 100.0 | 5000.0 | 50,000 |

The excipients used as listed above were pharmaceutical-grade and met USP standards.

Ivermectin was first dissolved in MCT oil using a propeller mixer and appropriately sized vessel. An extra 10% ivermectin and MCT oil was weighed out in order to prepare a 10% ivermectin/MCT oil overage solution. Potassium sorbate and anhydrous citric acid were milled through a rotating impeller mill (Comil®) equipped with a 2A024R screen. The dry ingredients, flavoring agent, pyrantel pamoate, DCPD, and sodium stearyl fumarate, were de-clumped or sieved though a 20-mesh screen. The milled potassium sorbate and anhydrous citric acid, the de-lumped dry ingredients, microcrystalline cellulose, and croscarmellose sodium were loaded into a plow mixer and mixed for 2 minutes at 100 rpm. The DL-α-tocopheryl acetate was added to the vessel containing glycerin and manually mixed with a spatula for 1 minute. With the plow mixer operating at 100 rpm, the glycerin/DL-α-tocopheryl acetate mixture was added to the mixing blend (time of addition=2 minutes). After the entire quantity of glycerin/DL-α-tocopheryl acetate was added, the blend was mixed for 1 additional minute. With the plow mixer operating at 100 rpm, the precise amount of ivermectin/MCT oil solution was added to the mixture (time of addition=2 minutes). The plow mixer was opened and visually inspected for residues stuck to the wall and the plows of the mixer. The residues were scraped from the wall and plows of the mixer and returned to the center of the mixer. The blend was mixed at room temperature until the material achieved a dough-like consistency (approximately 15 minutes). The wet mass was discharged from the plow mixer and loaded into the hopper of a ribbon-forming machine (Vemag Robot 500™ portioner). Ribbons with length of about 15" were formed at room temperature and placed on parchment lined trays. The ribbons were cured at room temperature for 18-24 hours. Then the ribbons were cut into 5 g±0.25 g segments using a dedicated tool to provide the final dose weight of ivermectin (136 µg) and pyrantel (114 mg). The portions were then cured at room temperature for 72 hours (3 days) prior to bulk packaging.

The whole process above was carried out under ambient room-temperature conditions without heating or cooling required. In addition, the batch size was significantly increased (i.e., 50 times) from the batch size used for the same formulation in Example 5.

Example 14—Dissolution Profile of Soft Chew D

Ivermectin/Pyrantel (136 µg/114 mg) Soft Chews

TABLE 14

Dissolution Profile of Soft Chew D

| Time (min) | Day 3 | | Day 3 + 2 Weeks | | Day 3 + 4 Weeks | |
|---|---|---|---|---|---|---|
| | Ivermectin (% dissolved) | Pyrantel (% dissolved) | Ivermectin (% dissolved) | Pyrantel (% dissolved) | Ivermectin (% dissolved) | Pyrantel (% dissolved) |
| 10 | 14 | 13 | 24 | 21 | 21 | 17 |
| 20 | 26 | 26 | 44 | 39 | 36 | 31 |
| 30 | 35 | 37 | 59 | 54 | 52 | 45 |
| 45 | 51 | 52 | 78 | 73 | 70 | 61 |
| 60 | 58 | 63 | 92 | 88 | 82 | 75 |
| 90 | 69 | 77 | 103 | 99 | 99 | 90 |
| 120 | 85 | 91 | 107 | 101 | 105 | 95 |
| 180 | 93 | 99 | 109 | 100 | 107 | 96 |

Dissolution Conditions: 4% SLS in water, Volume 1000 ml, 75 rpm, 37.0° C. ± 0.5° C.

The soft chews of Example 13 (Soft Chew D, 5 g per chew) were stored at 25° C. and 60% relative humidity (RH) for 4 weeks. The dissolution tests were carried out under the conditions indicated above for each API (ivermectin and pyrantel) at time-points of Day 3, Day 3+2 weeks, and Day 3+4 weeks. Samples were withdrawn at various time intervals to generate a dissolution profile at each given time-point. As shown in Table 14 above, the dissolution profiles of each API remained fast and consistent with no major changes after the 4-week time-period.

Example 15—Stability of Soft Chew D

Ivermectin/Pyrantel (136 µg/114 mg) Soft Chews

TABLE 15

Stability of Soft Chew D

| Test Method | Time 0 | 1 Month | 2 Months | 3 Months |
|---|---|---|---|---|
| Moisture - Karl Fischer | 4 | 3.8 | 3.9 | 3.4 |
| Average Weight - Gravimetric | 5.22 | 5.17 | 5.14 | 5.19 |
| Ivermectin Assay - HPLC | 102.8 | 95.5 | 96.2 | 98.9 |
| Pyrantel Assay - HPLC | 102.0 | 100.2 | 100.2 | 100.5 |

The bulk drug product was placed in a 16"×24"×4" parchment paper lined fiber box containing approximately 4.5 kg of chews and stored in warehouse conditions. The soft chews were tested for moisture content, average weight, ivermectin assay and pyrantel assay over 3 months. As shown in Table 15, all of the test results remained stable over time.

Example 16—Texture of Soft Chew D Over Time

Ivermectin/Pyrantel (136 µg/114 mg) Soft Chews

TABLE 16

Texture of Soft Chew D over Time

| Day | Texture* (N) |
|---|---|
| 3 | 9.2 |
| 3 + 2 weeks | 13 |
| 3 + 4 weeks | 12 |

*Texture is measured as the peak force (in Newtons) necessary to push a sphere of ¼ inch diameter to a depth of 2.0 mm into the soft chew with a velocity of 1.0 mm/sec.

The soft chews were allowed to cure at ambient conditions over a period of 4 weeks. The texture of the soft chews was measured on day 3, day 3+2 weeks, and day 3+4 weeks after manufacture. As shown in Table 16, the soft chews remained soft and malleable over time.

Example 17—Preparation of Soft Chew E

Ivermectin/Pyrantel (272 µg/227 mg) Soft Chews

TABLE 17

Composition of Soft Chew E

| Ingredients | % (w/w) | mg/chew | Batch Size (g) |
|---|---|---|---|
| Ivermectin | 0.00272 | 0.272 mg (272 µg) | 1.360 |
| Pyrantel Pamoate | 6.572 | 657.2 (227 mg Pyrantel) | 3,286.0 |
| DCPD | 29.0 | 2900.0 | 14,500.0 |
| MCC | 10.0 | 1000.0 | 5,000.0 |
| Flavoring agent | 20.0 | 2000.0 | 10,000.0 |
| Croscarmellose Sodium | 1.5 | 150.0 | 750.0 |
| Glycerin | 26.0 | 2600.0 | 13,000.0 |
| MCT | 4.575 | 457.5 | 2287.5 |
| Sodium Stearyl Fumarate | 1.5 | 150.0 | 750.0 |
| Anhydrous Citric Acid | 0.5 | 50.0 | 250.0 |
| Potassium Sorbate | 0.3 | 30.0 | 150.0 |
| DL-α-Tocopheryl Acetate | 0.05 | 5.0 | 25.0 |
| TOTAL | 100.0 | 10,000.0 | 50,000 |

The excipients used as listed above were pharmaceutical-grade and met USP standards.

Ivermectin was first dissolved in MCT oil using a propeller mixer and appropriately sized vessel. An extra 10% ivermectin and MCT oil was weighed out in order to prepare a 10% ivermectin/MCT oil overage solution. Potassium sorbate and anhydrous citric acid were milled through a rotating impeller mill (Comil®) equipped with a 2A024R screen. The dry ingredients, flavoring agent, pyrantel pamoate, DCPD, and sodium stearyl fumarate, were de-clumped or sieved though a 20-mesh screen. The milled potassium sorbate and anhydrous citric acid, the de-lumped dry ingredients, microcrystalline cellulose and croscarmellose sodium were loaded into a plow mixer and mixed for 2 minutes at 100 rpm. The DL-α-tocopheryl acetate was added to the vessel containing glycerin and manually mixed with a spatula for 1 minute. With the plow mixer operating at 100 rpm, the glycerin/DL-α-tocopheryl acetate mixture was added to the mixing blend (time of addition=2 minutes). After the entire quantity of glycerin/DL-α-tocopheryl acetate was added, the blend was mixed for 1 additional minute. With the plow mixer operating at 100 rpm, the precise amount of ivermectin/MCT oil solution was added to the mixture (time of addition=2 minutes). The plow mixer was opened and visually inspected for residues stuck to the wall and the plows of the mixer. The residues were scraped from the wall and plows of the mixer and returned to the center of the mixer. The blend was mixed at room temperature until the material achieved a dough-like consistency (approximately 15 minutes). The wet mass was discharged from the plow mixer and loaded into the hopper of a ribbon-forming machine (Vemag Robot 500™ portioner). Ribbons with length of about 15" were formed at room temperature and placed on parchment lined trays. The ribbons were cured at room temperature for 18-24 hours. Then the ribbons were cut into 10 g±0.5 g segments using a dedicated tool to provide the final dose weight of ivermectin (272 µg) and pyrantel (227 mg). The portions were then cured at room temperature for 72 hours (3 days) prior to bulk packaging.

The whole process above was carried out under ambient room-temperature conditions without heating or cooling required. In addition, the batch size was significantly increased (i.e., 50 times) from the batch size used for the same formulation in Example 5.

Example 18—Dissolution Profile of Soft Chew E

Ivermectin/Pyrantel (272 µg/227 mg) Soft Chews

TABLE 18

| | Dissolution Profile of Soft Chew E | | | | | |
|---|---|---|---|---|---|---|
| | Day 3 | | Day 3 + 2 Weeks | | Day 3 + 4 Weeks | |
| Time (min) | Ivermectin (% dissolved) | Pyrantel (% dissolved) | Ivermectin (% dissolved) | Pyrantel (% dissolved) | Ivermectin (% dissolved) | Pyrantel (% dissolved) |
| 10 | 9 | 7 | 15 | 17 | 14 | 17 |
| 20 | 23 | 16 | 29 | 30 | 27 | 33 |
| 30 | 35 | 25 | 41 | 45 | 41 | 47 |
| 45 | 47 | 38 | 56 | 61 | 57 | 64 |
| 60 | 62 | 50 | 67 | 72 | 71 | 77 |
| 90 | 82 | 69 | 87 | 90 | 82 | 92 |
| 120 | 99 | 83 | 96 | 101 | 88 | 101 |
| 180 | 108 | 94 | 105 | 105 | 91 | 105 |

Dissolution Conditions: 4% SLS in water, Volume 2000 ml, 75 rpm, 37.0° C. ± 0.5° C.

The soft chews of Example 17 (Soft Chew E, 10 g per chew) were stored at 25° C. and 60% relative humidity (RH) for 4 weeks. The dissolution tests were carried out under the conditions indicated above for each API (ivermectin and pyrantel) at time-points of Day 3, Day 3+2 weeks, and Day 3+4 weeks. Samples were withdrawn at various time intervals to generate a dissolution profile at each given time-point. As shown in Table 18 above, the dissolution profiles of each API remained fast and consistent with no major changes after the 4-week time-period.

Example 19—Texture of Soft Chew E Over Time

Ivermectin/Pyrantel (272 µg/227 mg) Soft Chews

TABLE 19

| Texture of Soft Chew E over Time | |
|---|---|
| Day | Texture * (N) |
| 3 | 8.9 |
| 3 + 2 weeks | 14 |
| 3 + 4 weeks | 14 |

* Texture is measured as the peak force (in Newtons) necessary to push a sphere of ¼ inch diameter to a depth of 2.0 mm into the soft chew with a velocity of 1.0 mm/sec.

The soft chews were allowed to cure at ambient conditions over a period of 4 weeks. The texture of the soft chews was measured on day 3, day 3+2 weeks and day 3+4 weeks after manufacture. As shown in Table 19, the soft chews remained soft and malleable over time.

Example 20—Microbiological Examination of Soft Chew E

Ivermectin/Pyrantel (272 µg/227 mg) Soft Chews

TABLE 20

| Microbiological Examination of Soft Chew E | | | | |
|---|---|---|---|---|
| | Parameter | | | |
| Test | Method | Specification | Result | Status |
| Total Aerobic Microbial Count | USP <61> | NMT 1000 CFU/g | <100 CFU/g | Pass |

TABLE 20-continued

| Microbiological Examination of Soft Chew E | | | | |
|---|---|---|---|---|
| | Parameter | | | |
| Test | Method | Specification | Result | Status |
| Total Combined Yeasts and Molds Count | USP <61> | NMT 1000 CFU/g | <100 CFU/g | Pass |
| E. coli | USP <62> | Absent | Absent | Pass |

The soft chews were tested for microbiological level according to the methods described in the United States Pharmacopeia, USP <61> and USP <62>. As shown in Table 20, the microbiological level in the soft chews was acceptable.

Example 21—Preparation of Soft Chew F

Placebo Soft Chews

TABLE 21

| Composition of Soft Chew F | | |
|---|---|---|
| Ingredients | % (w/w) | mg/chew |
| DCPD | 25.0 | 2500.0 |
| MCC | 8.0 | 800.0 |
| Flavoring Agent (FlavorPal ™) | 30.0 | 3000.0 |
| Croscarmellose Sodium | 5.0 | 500.0 |

TABLE 21-continued

Composition of Soft Chew F

| Ingredients | % (w/w) | mg/chew |
|---|---|---|
| Glycerin | 25.0 | 2500.0 |
| MCT | 5.0 | 500.0 |
| Magnesium Stearate | 2.0 | 200.0 |
| TOTAL | 100.0 | 10,000 |

The excipients used as listed above were pharmaceutical-grade and met USP standards.

The dry ingredients, flavoring agent, DCPD, MCC, croscarmellose sodium and magnesium stearate, were de-clumped or sieved though a 20-mesh screen. The screened dry ingredients were then tumble-blended for about 2 minutes. The mixed dry ingredients were then loaded into a low-shear planetary mixer (Globe SP8™—Globe Food Equipment Company, Dayton, Ohio, USA). While operating the mixer, glycerin was added to the mixing blend (time of addition=2 minutes). After the addition of glycerin, MCT oil was added to the mixture under continuous mixing (time of addition=2 minutes). All components were mixed at ambient conditions until the material achieved a dough-like consistency (approximately 17 minutes). The wet mass was then moved to a ribbon forming machine. Ribbons with length of about 25 cm were formed at ambient conditions. The ribbons were cured at room temperature for 24 hours. Then the ribbons were portioned into 10 g±0.5 g segments.

The whole process above was carried out under ambient room-temperature conditions without heating or cooling required.

Example 22—Texture of Soft Chew F

Placebo Soft Chews

TABLE 22

Texture of Soft Chew F

| Day | Disintegration Time (min:sec) | Texture* (N) |
|---|---|---|
| 0 | 47:24 | 0.4 |
| 1 | 40:27 | 3.4 |
| 7 | 46:33 | 7.2 |
| 14 | 45:55 | 8.4 |

*Texture is measured as the peak force (in Newton) necessary to push a sphere of 5.0 mm in diameter to a depth of 2.0 mm into the soft chew with a velocity of 1.0 mm/sec.

The soft chews were allowed to cure at ambient conditions over a period of 14 days. The disintegration and texture of the soft chews was measured on the same day of manufacture (day 0) and on day 1, day 7, and day 14 after manufacture. As shown in Table 22, the soft chews retained its fast disintegration time and remained soft and malleable over time.

Example 23—Preparation of Soft Chew G

Placebo Soft Chews

TABLE 23

Composition of Soft Chew G

| Ingredients | % (w/w) | mg/chew |
|---|---|---|
| DCPD | 30.0 | 3000.0 |
| MCC | 10.0 | 1000.0 |
| Flavoring Agent (FlavorPal ™) | 23.0 | 2300.0 |
| Croscarmellose Sodium | 5.0 | 500.0 |
| Glycerin | 25.0 | 2500.0 |
| MCT | 5.0 | 500.0 |
| Magnesium Stearate | 2.0 | 200.0 |
| TOTAL | 100.0 | 10,000 |

The excipients used as listed above were pharmaceutical-grade and met USP standards.

The dry ingredients, flavoring agent, DCPD, MCC, croscarmellose sodium and magnesium stearate, were de-clumped or sieved though a 20-mesh screen. The screened dry ingredients were then tumble-blended for about 2 minutes. The mixed dry ingredients were then loaded into a low-shear planetary mixer (Globe SP8™—Globe Food Equipment Company, Dayton, Ohio, USA). While operating the mixer, glycerin was added to the mixing blend (time of addition=2 minutes). After the addition of glycerin, MCT oil was added to the mixture under continuous mixing (time of addition=2 minutes). All components were mixed at ambient conditions until the material achieved a dough-like consistency (approximately 19 minutes). The wet mass was then moved to a ribbon forming machine. Ribbons with length of about 25 cm were formed at ambient conditions. The ribbons were cured at room temperature for 24 hours. Then the ribbons were portioned into 10 g±0.5 g segments.

The whole process above was carried out under ambient room-temperature conditions without heating or cooling required.

Example 24—Texture of Soft Chew G

Placebo Soft Chews

TABLE 24

Texture of Soft Chew G

| Day | Disintegratian Time (min:sec) | Texture* (N) |
|---|---|---|
| 0 | 36:23 | 0.4 |
| 1 | 37:28 | 2.9 |
| 7 | 44:05 | 8.3 |
| 14 | 40:50 | 10.0 |

*Texture is measured as the peak force (in Newton) necessary to push a sphere of 5.0 mm in diameter to a depth of 2.0 mm into the soft chew with a velocity of 1.0 mm/sec.

The soft chews were allowed to cure at ambient conditions over a period of 14 days. The disintegration and texture of the soft chews was measured on the same day of manufacture (day 0) and on day 1, day 7, and day 14 after manufacture. As shown in Table 24, the soft chews retained its fast disintegration time and remained soft and malleable over time.

All publications, patents, and patent applications are herein incorporated by reference in their entirety to the same extent as if each individual publication, patent, or patent application was specifically and individually indicated to be incorporated by reference in its entirety.

While certain embodiments have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the compositions and methods described herein. While the foregoing invention has been described in some detail for purposes of clarity and understanding, it will be appreciated by one skilled in the art, from a reading of the disclosure, that various changes in form and detail can be made without departing from the true scope of the invention in the appended claims

What is claimed is:

1. A starch-free soft chew formulation for oral delivery of at least one active ingredient to an animal, the formulation comprising non-starch solid excipients, non-water liquid excipients, and at least one active ingredient,
the non-starch solid excipients comprising at least:
dibasic calcium phosphate, and
microcrystalline cellulose, and
the non-water liquid excipients comprising at least:
glycerin, and
triglycerides of fatty acids with carbon chain lengths of at least C6, in an amount of at least 2% w/w of the formulation,
wherein:
the formulation contains no starch,
the formulation contains no water as an excipient and no added water, and
the formulation contains no filler or bulking agent other than the dibasic calcium phosphate and microcrystalline cellulose.

2. The soft chew formulation of claim 1, wherein the non-starch solid excipients and non-water liquid excipients further comprise at least one of a flavoring, a binder, a disintegrant, and a surfactant.

3. The soft chew formulation of claim 1, wherein the dibasic calcium phosphate is hydrous.

4. The soft chew formulation of claim 3, wherein the dibasic calcium phosphate is dibasic calcium phosphate dihydrate.

5. The soft chew formulation of claim 1, wherein the weight ratio of the dibasic calcium phosphate to the microcrystalline cellulose is about 1.1 to 4:1 or about 2:1 to 3:1.

6. The soft chew formulation of claim 1, wherein the triglycerides of fatty acids are caprylic/capric triglycerides or medium-chain triglycerides with carbon chain lengths of C6-C12.

7. The soft chew formulation of claim 6, wherein the weight ratio of the glycerin to the triglycerides of fatty acids is about 4:1 to 7:1 or about 5:1 to 6:1.

8. The soft chew formulation of claim 1, wherein the non-starch solid excipients and non-water liquid excipients further comprise croscarmellose sodium, magnesium stearate, stearic acid, or sodium stearyl fumarate.

9. The soft chew formulation of claim 1, wherein the non-starch solid excipients and non-water liquid excipients further comprise citric acid.

10. The soft chew formulation of claim 9, wherein the citric acid is citric acid anhydrous.

11. The soft chew formulation of claim 1, wherein the non-starch solid excipients and non-water liquid excipients further comprise α-tocopherol.

12. The soft chew formulation of claim 1, wherein the α-tocopherol is DL-α-tocopheryl acetate.

13. The soft chew formulation of claim 1, wherein the non-starch solid excipients and non-water liquid excipients farther comprise povidone, hydroxyl propyl cellulose, or hydroxyl methyl cellulose.

14. The soft chew formulation of claim 1, wherein the glycerin is present in the formulation in an amount of 15-50% w/w, and the triglycerides of fatty acids are present in the formulation in an amount of 2-20% w/w.

15. The soft chew formulation of claim 14, wherein the weight ratio of the dibasic calcium phosphate dihydrate to the microcrystalline cellulose is about 2:1 to about 3:1.

16. The soft chew formulation of claim 14, wherein the weight ratio of the glycerin to the triglycerides of fatty acids is about 4:1 to 7:1 or about 5:1 to 6:1.

17. The soft chew formulation of claim 1, wherein:
the non-starch solid excipients and non-water liquid excipients thither comprise:
flavoring, at 5-35% w/w of the formulation;
croscarmellose sodium, at 0-15% w/w of the formulation; and
magnesium stearate or sodium stearyl fumarate, at 0-5% w/w of the formulation;
the dibasic calcium phosphate is dibasic calcium phosphate dihydrate and the triglycerides of fatty acids are medium-chain triglycerides; and
the weight percentages of the glycerin and the medium-chain triglycerides in the formulation are 15-50% w/w and 0.2-20% w/w, respectively.

18. The soft chew formulation of claim 17, wherein the dibasic calcium phosphate dihydrate, microcrystalline cellulose, flavoring, croscarmellose sodium, glycerin, medium-chain triglycerides, and magnesium stearate are in a weight ratio of about 25:8:30:5:25:5:2 or about 30:10:23:5:25:5:2, respectively.

19. The soft chew formulation of claim 17, wherein the non-starch solid excipients and non-water liquid excipients further comprise:
citric acid anhydrous, at 0-5% w/w of the formulation;
potassium sorbate, at 0.01-3% w/w of the formulation; and
DL-α-tocopheryl acetate, at 0.01-3% w/w of the formulation.

20. The starch-free soft chew formulation of claim 1, which has a texture value of 11 N or less 4 weeks after preparation, wherein said texture value is measured as a peak force necessary to push a sphere 5.0 mm in diameter to a depth of 2.0 mm into a soft chew weighing 2.5 g±0.13 g with a velocity of 1.0 mm/sec, and wherein the formulation contains:
2.5-6.5% w/w of the at least one active ingredient;
25-30% w/w of the dibasic calcium phosphate;
8-10% w/w of the microcrystalline cellulose;
25-28% w/w of the glycerin;
4.5-5% w/w of the triglycerides of fatty acids;
20-30% w/w of a flavoring agent;
1.5-5% w/w of croscarmellose sodium;
1.5-2% w/w of at least one of sodium stearyl fumarate and magnesium stearate; and
at least one of a preservative and an antioxidant.

21. A process for making the starch-free soft chew-formulation according to claim 1, said process comprising the steps of:
- a) dry-mixing the non-starch solid excipients in a mixer; and
- b) mixing the solid excipients into a dough-like material by adding into the mixer the non-water liquid excipients.

* * * * *